(12) United States Patent
Lee et al.

(10) Patent No.: US 8,920,946 B2
(45) Date of Patent: Dec. 30, 2014

(54) ORGANIC LIGHT-EMITTING COMPOUND AND ORGANIC LIGHT-EMITTING DEVICE INCLUDING THE SAME

(71) Applicant: Samsung Display Co., Ltd., Yongin-si (KR)

(72) Inventors: Jung-Sub Lee, Yongin-si (KR); Seung-Gak Yang, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 0 days.

(21) Appl. No.: 13/676,069

(22) Filed: Nov. 13, 2012

(65) Prior Publication Data

US 2014/0001443 A1    Jan. 2, 2014

(30) Foreign Application Priority Data

Jun. 29, 2012    (KR) .................. 10-2012-0071370

(51) Int. Cl.
| | | |
|---|---|---|
| *C07D 471/04* | (2006.01) | |
| *C07D 413/14* | (2006.01) | |
| *C07D 417/14* | (2006.01) | |
| *H01L 51/00* | (2006.01) | |

(52) U.S. Cl.
CPC ............ *C07D 471/04* (2013.01); *C07D 413/14* (2013.01); *C07D 417/14* (2013.01); *H01L 51/0032* (2013.01)
USPC ............. 428/690; 585/26; 549/456; 548/440; 544/180

(58) Field of Classification Search
None
See application file for complete search history.

(56) References Cited

U.S. PATENT DOCUMENTS

2004/0217697 A1 * 11/2004 Lee et al. ...................... 313/504
2011/0156014 A1    6/2011 Kim et al.

FOREIGN PATENT DOCUMENTS

| JP | 06-271846 | 9/1994 | | |
|---|---|---|---|---|
| JP | 2004-075750 | 3/2004 | | |
| JP | 2011-178742 | 9/2011 | | |
| JP | 2011178742 A | * 9/2011 | ........... | C07D 265/38 |
| KR | 10-2010-0024340 | 3/2010 | | |
| KR | 10-2011-0049217 | 5/2011 | | |
| WO | WO 2011-055911 A1 | 5/2011 | | |

OTHER PUBLICATIONS

Machine English translation of JP 2011-178742 A. Aug. 2, 2013.*

* cited by examiner

*Primary Examiner* — J. L. Yang
(74) *Attorney, Agent, or Firm* — Christie, Parker & Hale, LLP

(57) ABSTRACT

Embodiments of the present invention are directed to a compound represented by Formula 1 below and an organic light-emitting device including the compound.

Formula 1

19 Claims, 1 Drawing Sheet

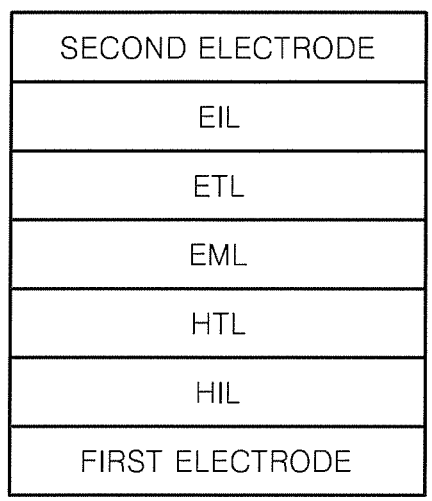

ORGANIC LIGHT-EMITTING COMPOUND AND ORGANIC LIGHT-EMITTING DEVICE INCLUDING THE SAME

CROSS-REFERENCE TO RELATED PATENT APPLICATION

This application claims priority to and the benefit of Korean Patent Application No. 10-2012-0071370, filed on Jun. 29, 2012 in the Korean Intellectual Property Office, the entire content of which is incorporated herein by reference.

BACKGROUND

1. Technical Field

The present invention relates to a compound for organic light-emitting devices, and an organic light-emitting device including the compound.

2. Description of the Related Art

Organic light-emitting devices (OLEDs) are self-emitting devices having wide viewing angles, good contrast, quick response speeds, high brightness, and good driving voltage characteristics. Also, OLEDs can provide multicolored images.

A typical OLED has a structure including a substrate, and an anode, a hole transport layer (HTL), an emission layer (EML), an electron transport layer (ETL), and a cathode sequentially stacked on the substrate. In this regard, the HTL, the EML, and the ETL are organic thin films formed of organic compounds.

An operating principle of an OLED having the above-described structure is as follows.

When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

A major factor affecting luminescent efficiency of an OLED is the luminescent material. Although fluorescent materials have been widely used as the luminescent material, development of a phosphorescent material capable of improving luminescent efficiency up to four times based on theoretical electroluminescence mechanisms would be an effective method for improving luminescent efficiency.

Currently, 4,4'-bis(carbazol-9-yl)biphenyl (CBP) is a known phosphorescent host material. High-efficiency organic light-emitting devices with hole blocking layers formed from 2,9-dimethyl-4,7-diphenyl-1,10-phenanthroline (BCP) or BAlq, and high-performance OLEDs using a BAlq derivative as a host are also known.

Although they have advantageous light-emitting characteristics, these existing luminescent materials have low glass transition temperatures and poor thermal stability, and thus may deteriorate during high-temperature deposition processes conducted under vacuum. The power efficiency of an OLED may be represented as: Power efficiency=(π/Voltage)×Current Efficiency. That is, the power efficiency is inversely proportional to voltage, and the power efficiency of the OLED should be high in order to reduce power consumption. In practice, OLEDs using common phosphorescent (host) materials, such as BAlq or CBP, may have higher driving voltages, but considerably higher current efficiency (cd/A), as compared with OLEDs using fluorescent materials, and thus are not advantageous in terms of power efficiency (lm/w). OLEDs using such existing host materials are also not satisfactory in terms of lifetime.

SUMMARY

Embodiments of the present invention are directed to a novel organic light-emitting compound with a rigid backbone having improved luminescent efficiency and lifetime as compared with existing host materials, as well as appropriate color coordinates. Other embodiments of the present invention are directed to high-efficiency, long lifetime organic light-emitting devices using the organic light-emitting compound.

According to an aspect of the present invention, a compound is represented by Formula 1 below.

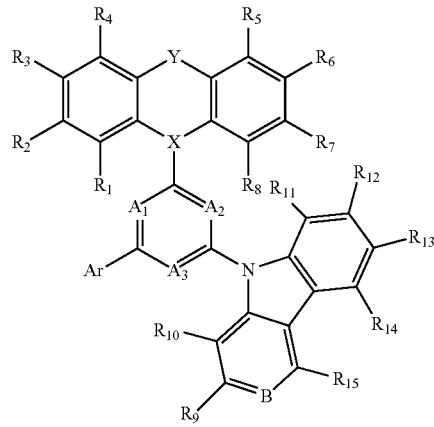

Formula 1

In Formula 1, $A_1$ to $A_3$ are each independently N, O, S, or $C(R_{20})$. X and Y are each independently N, O, or S. B is N or $C(R_{21})$. Ar is a substituted or unsubstituted $C_6$-$C_{60}$ aryl group or a substituted or unsubstituted $C_3$-$C_{30}$ hetero aryl group. $R_1$ to $R_{15}$, $R_{20}$, and $R_{21}$ are each independently a hydrogen atom, a deuterium atom, a substituted or unsubstituted C1-C60 alkyl group, a substituted or unsubstituted C3-C60 cycloalkyl group, a substituted or unsubstituted C6-C60 aryl group, or a substituted or unsubstituted C3-C60 heteroaryl group. Optionally, $R_{15}$ and $R_{21}$ may be linked to form a ring.

According to another aspect of the present invention, an organic light-emitting device includes: a first electrode; a second electrode; and an organic layer between the first electrode and the second electrode. The organic layer includes the above-described compound.

According to another aspect of the present invention, a flat panel display device includes the above-described organic light-emitting device, in which the first electrode of the organic light-emitting device is electrically connected to a source electrode or a drain electrode of a thin-film transistor.

BRIEF DESCRIPTION OF THE DRAWING

The above and other features and advantages of the present invention will become more apparent by reference to the following detailed description when considered in conjunction with the attached drawing in which:

FIG. 1 is a schematic of the structure of an organic light-emitting device according to an embodiment of the present invention.

DETAILED DESCRIPTION

As used herein, the term "and/or" includes any and all combinations of one or more of the associated listed items. Expressions such as "at least one of," when preceding a list of elements, modify the entire list of elements and do not modify the individual elements of the list.

According to an aspect of the present invention, an organic light-emitting compound is represented by Formula 1 below.

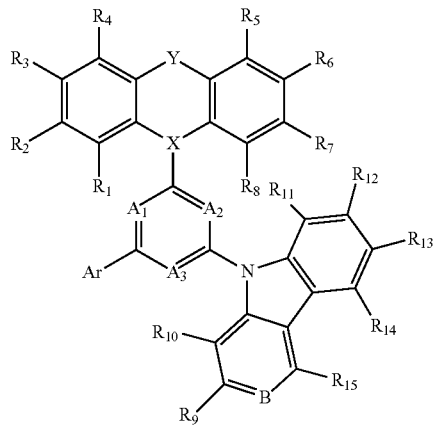

Formula 1

In Formula 1, $A_1$ to $A_3$ are each independently N, O, S, or $C(R_{20})$. X and Y are each independently N, O, or S; B is N or $C(R_{21})$. Ar is a substituted or unsubstituted $C_6$-$C_{60}$ aryl group or a substituted or unsubstituted $C_3$-$C_{30}$ hetero aryl group. $R_1$ to $R_{15}$, $R_{20}$, and $R_{21}$ are each independently a hydrogen atom, a deuterium atom, a substituted or unsubstituted C1-C60 alkyl group, a substituted or unsubstituted C3-C60 cycloalkyl group, a substituted or unsubstituted C6-C60 aryl group, or a substituted or unsubstituted C3-C60 heteroaryl group. $R_{15}$ and $R_{21}$ may optionally be linked to form a ring.

According to embodiments of the present invention, the compound of Formula 1 may have improved luminescent efficiency and improved lifetime characteristics. Thus, an organic light-emitting device manufactured using the compound may have a long lifetime, and higher power efficiency with improved power consumption.

In the compound of Formula 1, the core moiety (i.e.,

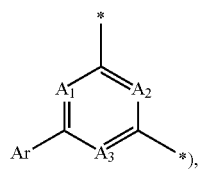

the moiety linked to the core (i.e.,

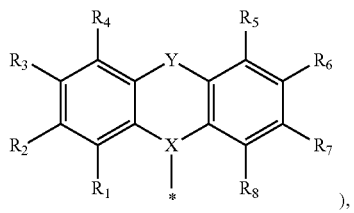

the moiety

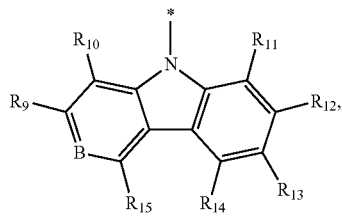

and Ar will now be described in greater detail.

In some embodiments, in Formula 1, the core moiety

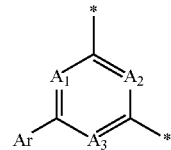

may be a moiety represented by one of the following formulae, wherein * indicates a binding site.

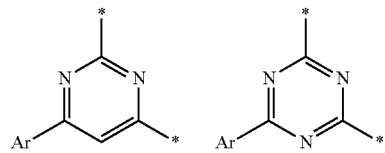

The core may provide the compound of Formula 1 with the ability to transport electrons.

In some embodiments, in Formula 1, the moiety

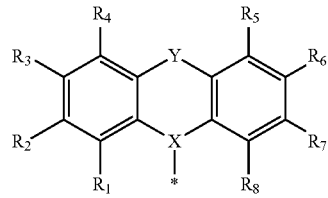

linked to the core may be a moiety represented by one of the following formulae, wherein * indicates a binding site.

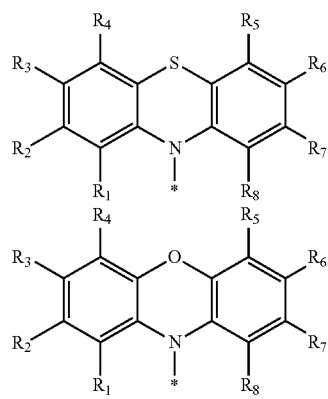

In some other embodiments, in Formula 1, the

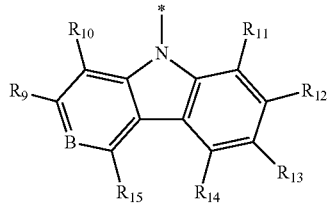

moiety may be a moiety represented by one of the following formulae.

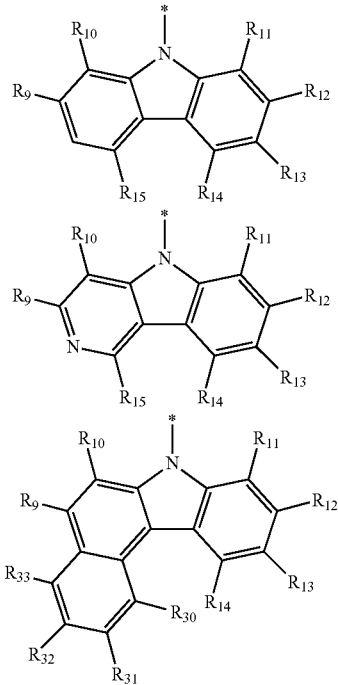

In the formulae above, $R_{30}$ to $R_{33}$ may be each independently a hydrogen atom, a deuterium atom, a substituted or unsubstituted C1-C60 alkyl group, a substituted or unsubstituted C3-C60 cycloalkyl group, a substituted or unsubstituted C6-C60 aryl group, or a substituted or unsubstituted C3-C60 heteroaryl group. Also, and * indicates a binding site.

In the carbazole analogue moiety, the N at the 9 position of the carbazole moiety is directly linked to the core, so that excitons may be generated with an increased bandgap level and a T1 energy level of about 2.5 eV or greater, which is advantageous for a phosphorescent host. Due to this advantage, the compound is more suitable for use as a host in the EML rather than in the HTL.

The carbazole analogue moiety may provide the compound of Formula 1 with the ability to transport holes.

Due to the core and carbazole analogue moieties in Formula 1, the compound of Formula 1 may have the ability to transport both electrons and holes, and thus may be used as a light-emitting material.

In some other embodiments, in Formula 1, Ar may be a compound represented by one of the following formulae, wherein * indicates a binding site.

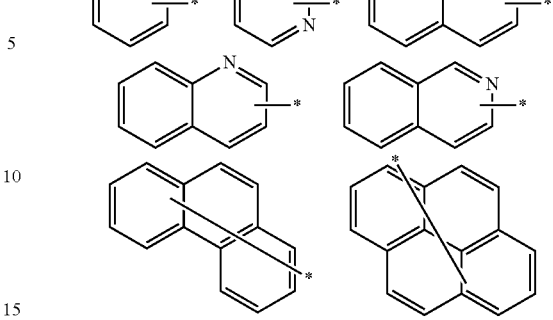

In some embodiments, in Formula 1 above, $R_1$ to $R_8$ may be each independently a hydrogen atom or a deuterium atom; and $R_9$ to $R_{15}$, and $R_{21}$ may be each independently a hydrogen atom, a deuterium atom, or a substituted or unsubstituted C6-C60 aryl group.

Hereinafter, substituents described with reference to the formulae will now be described in detail. In this regard, the numbers of carbon atoms in the substituents are presented only for illustrative purposes and do not limit the characteristics of the substituents.

The unsubstituted $C_1$-$C_{60}$ alkyl group, as used herein, refers to a linear or branched group. Examples of the alkyl group may include, but are not limited to, a methyl group, an ethyl group, a propyl group, an isobutyl group, a sec-butyl group, a pentyl group, an iso-amyl group, a hexyl group, a heptyl group, an octyl group, a nonanyl group, and a dodecyl group. To obtain the substituted $C_1$-$C_{60}$ alkyl group, at least one hydrogen atom of the alkyl group may be substituted with a heavy hydrogen atom, a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, or a $C_4$-$C_{16}$ heteroaryl group.

The unsubstituted $C_2$-$C_{60}$ alkenyl group indicates an unsaturated alkyl group having at least one carbon-carbon double bond in the center or at a terminal end of the alkyl group. Examples of the alkenyl group include an ethenyl group, a propenyl group, a butenyl group, and the like. To obtain the substituted $C_2$-$C_{60}$ alkenyl group, at least one hydrogen atom in the unsubstituted alkenyl group may be substituted with the substituents described above in connection with the alkyl group.

The unsubstituted $C_2$-$C_{60}$ alkynyl group indicates an alkyl group having at least one carbon-carbon triple bond in the center or at a terminal end of the alkyl group. Examples of the unsubstituted $C_2$-$C_{20}$ alkynyl group include acetylene, propylene, phenylacetylene, naphthylacetylene, isopropylacetylene, t-butylacetylene, diphenylacetylene, and the like. To obtain the substituted $C_2$-$C_{60}$ alkynyl group, at least one hydrogen atom in the alkynyl group may be substituted with the substituents described above in connection with the alkyl group.

The unsubstituted $C_3$-$C_{60}$ cycloalkyl group indicates a $C_3$-$C_{60}$ cyclic alkyl group. To obtain the substituted $C_3$-$C_{60}$ cycloalkyl group, at least one hydrogen atom in the cycloalkyl group may be substituted with the substituents described above in connection with the $C_1$-$C_{60}$ alkyl group.

The unsubstituted $C_1$-$C_{60}$ alkoxy group indicates a group having a structure of —OA where A is an unsubstituted $C_1$-$C_{60}$ alkyl group as described above. Non-limiting examples of the unsubstituted $C_1$-$C_{60}$ alkoxy group include a methoxy group, an ethoxy group, a propoxy group, an isopropyloxy group, a butoxy group, and a pentoxy group. To obtain the substituted $C_1$-$C_{60}$ alkoxy group, at least one hydrogen atom of the alkoxy group may be substituted with the substituents described above in connection with the alkyl group.

The unsubstituted $C_6$-$C_{60}$ aryl group indicates a carbocyclic aromatic system containing at least one ring. At least two rings may be fused to each other or linked to each other by a single bond. The term 'aryl' refers to an aromatic system, such as phenyl, naphthyl, or anthracenyl. To obtain the substituted $C_6$-$C_{60}$ aryl group, at least one hydrogen atom in the aryl group may be substituted with the substituents described above in connection with the unsubstituted $C_1$-$C_{60}$ alkyl group.

Non-limiting examples of the substituted or unsubstituted $C_6$-$C_{60}$ aryl group include a phenyl group, a $C_1$-$C_{10}$ alkylphenyl group (for example, ethylphenyl group), a halophenyl group (for example, o-, m-, and p-fluorophenyl groups, diehlorophenyl groups), a cyanophenyl group, a dicyanophenyl group, a trifluoromethoxyphenyl group, a biphenyl group, a halobiphenyl group, a cyanobiphenyl group, a $C_1$-$C_{10}$ alkyl biphenyl group, a $C_1$-$C_{10}$ alkoxybiphenyl group, an o-, m-, or p-toryl group, an o-, m-, or p-cumenyl group, a mesityl group, a phenoxyphenyl group, an (α,α-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (for example, fluoronaphthyl group), a $C_1$-$C_{10}$ alkylnaphthyl group (for example, methylnaphthyl group), a $C_1$-$C_{10}$ alkoxynaphthyl group (for example, methoxynaphthyl group), a cyanonaphthyl group, an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, and an ovalenyl group.

The unsubstituted $C_3$-$C_{60}$ heteroaryl group, as used herein, refers to aryl groups containing one, two or three hetero atoms selected from N, O, P and S. At least two rings may be fused to each other or linked to each other by a single bond. Examples of the unsubstituted $C_4$-$C_{60}$ heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolyl group, an isoquinolyl group, and a dibenzothiophene group. In addition, to obtain the substituted $C_3$-$C_{60}$ heteroaryl group, at least one hydrogen atom in the heteroaryl group may be substituted with the substituents described above in connection with the unsubstituted $C_1$-$C_{60}$ alkyl group.

The unsubstituted $C_5$-$C_{60}$ aryloxy group is a group represented by —$OA_1$ in which $A_1$ may be a $C_6$-$C_{60}$ aryl group. An example of the aryloxy group is a phenoxy group. To obtain the substituted $C_6$-$C_{60}$ aryloxy group, at least one hydrogen atom in the aryloxy group may be substituted with the substituents described above in connection with the unsubstituted $C_1$-$C_{60}$ alkyl group.

The unsubstituted $C_6$-$C_{60}$ arylthio group is represented by —$SA_1$ where $A_1$ may be a $C_6$-$C_{60}$ aryl group. Non-limiting examples of the arylthio group include a benzenethio group and a naphthylthio group. To obtain the substituted $C_6$-$C_{60}$ arylthio group, at least one hydrogen atom in the arylthio group may be substituted with the substituents described above in connection with the unsubstituted $C_1$-$C_{60}$ alkyl group.

The unsubstituted $C_6$-$C_{60}$ condensed polycyclic group, as used herein, refers to a substituent including at least two rings in which at least one aromatic ring and/or at least one non-aromatic ring are fused to each other, or refers to a substituent having an unsaturated group in a ring that may not form a conjugate structure. The unsubstituted $C_6$-$C_{60}$ condensed polycyclic group is distinct from the aryl group or heteroaryl group because it is non-aromatic.

Non-limiting examples of the compound represented by Formula 1 include Compounds 1 to 34 represented by the following formulae.

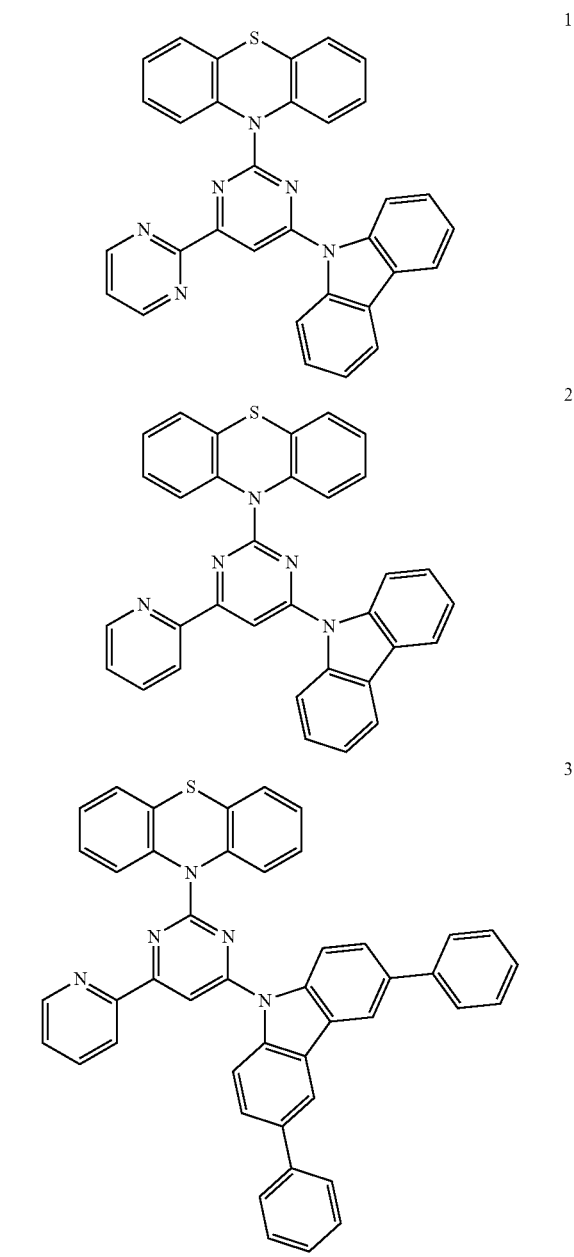

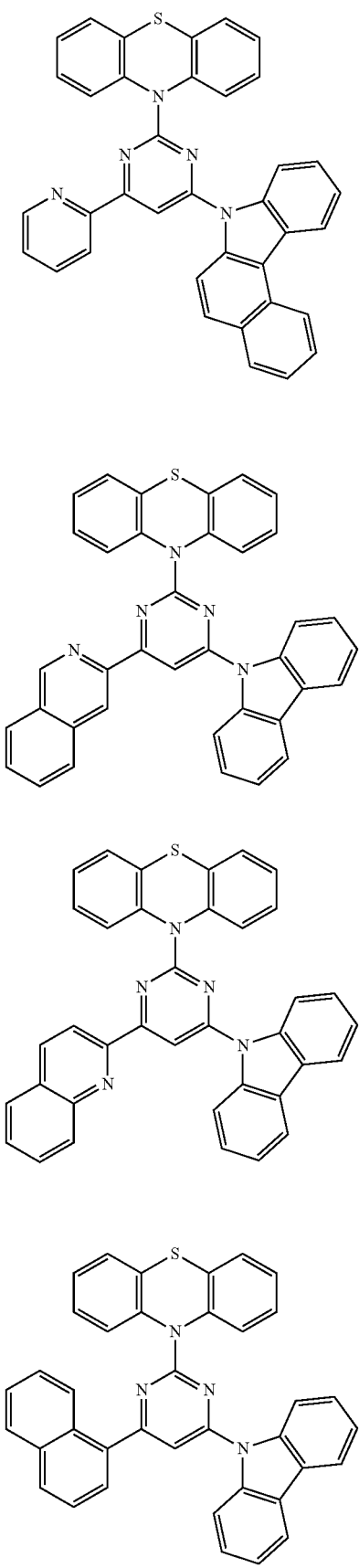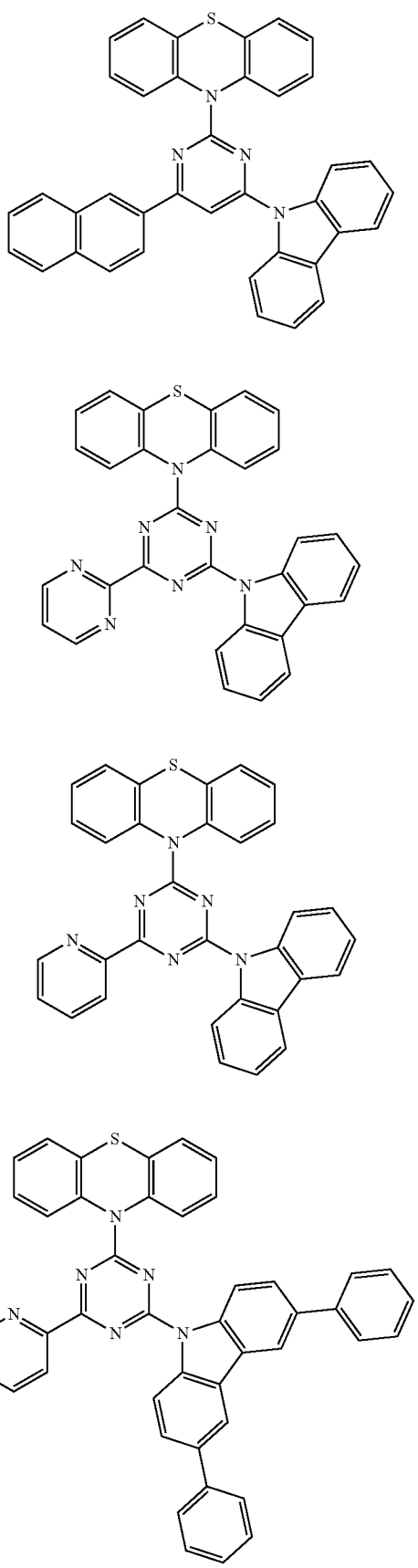

-continued
12
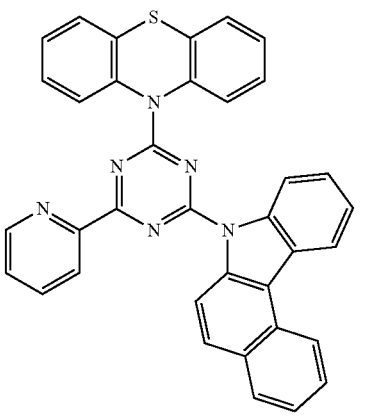
13
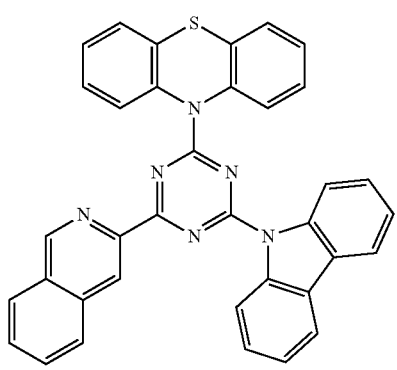
14
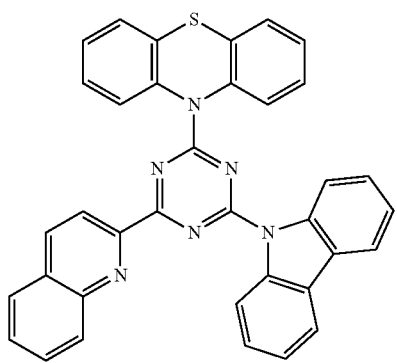
15
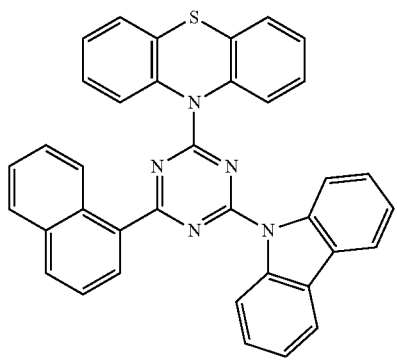
-continued
16
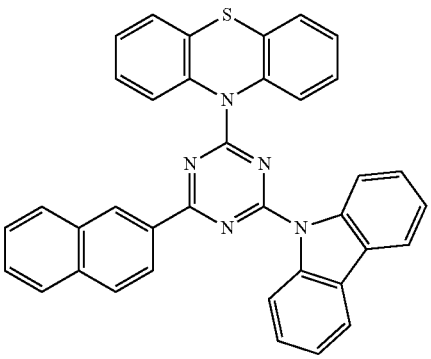
17
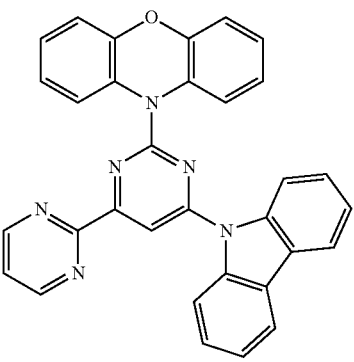
18
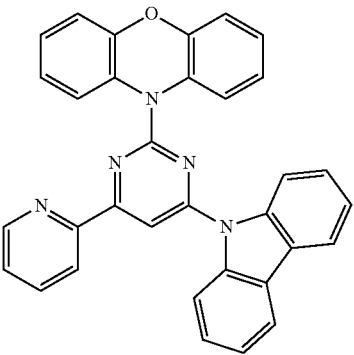
19
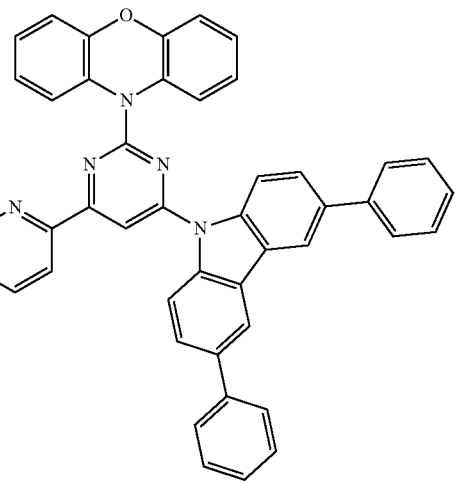

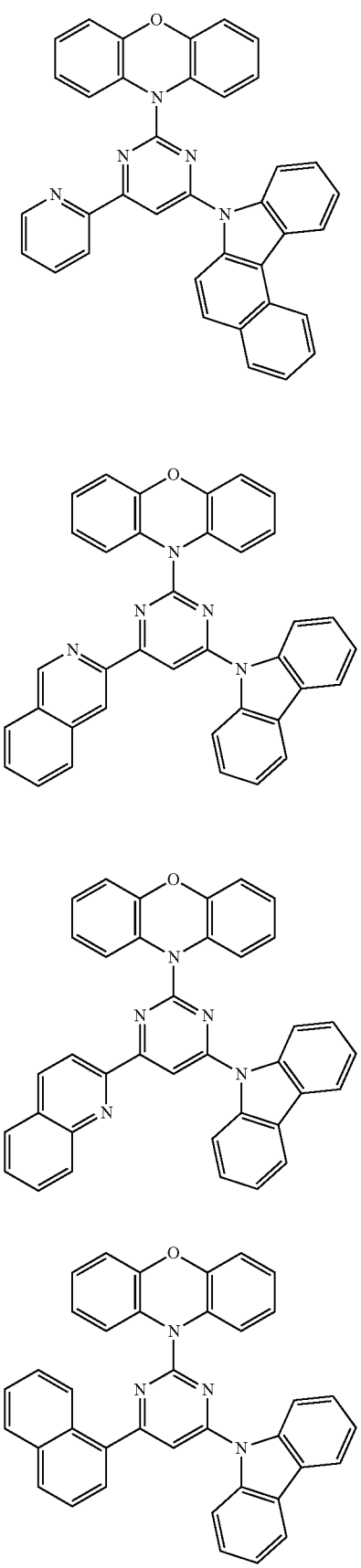
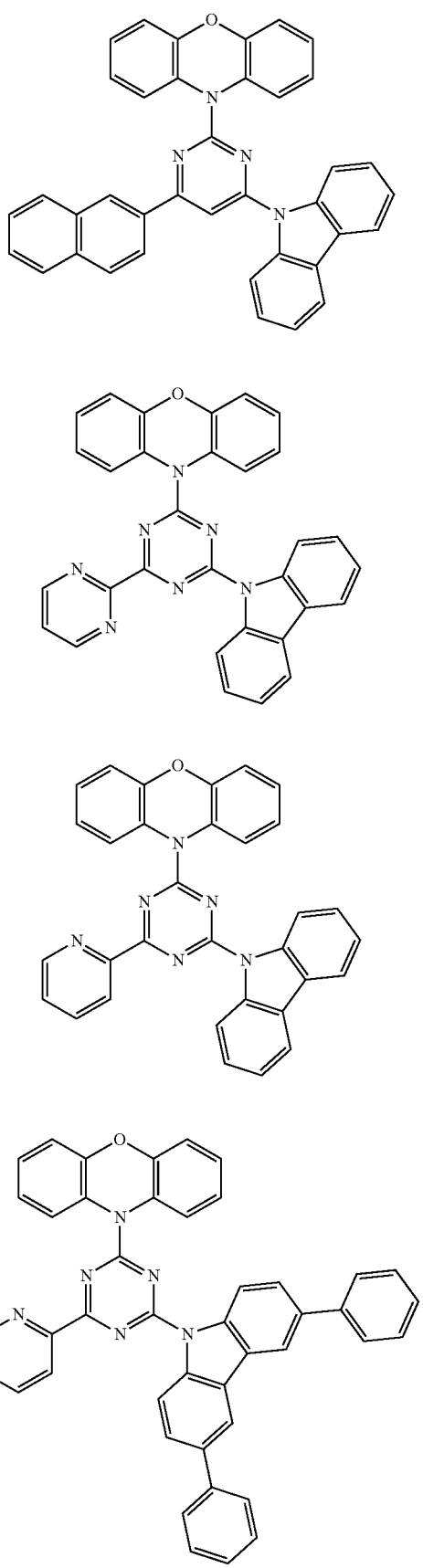

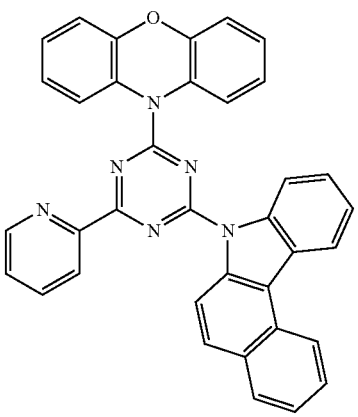

28

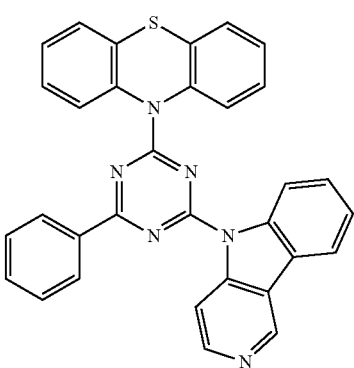

29

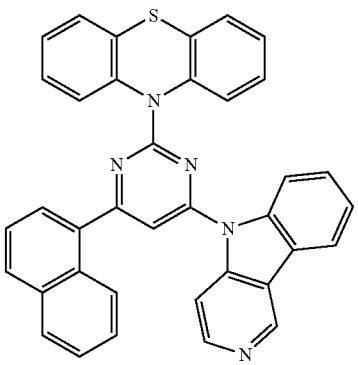

30

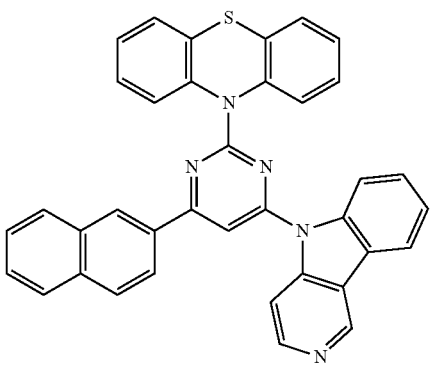

31

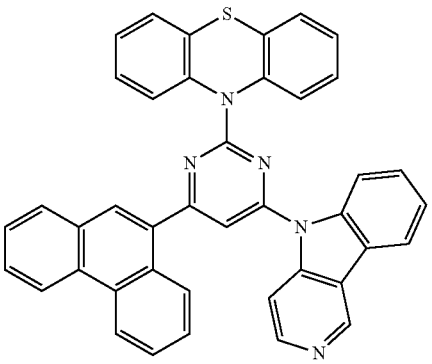

32

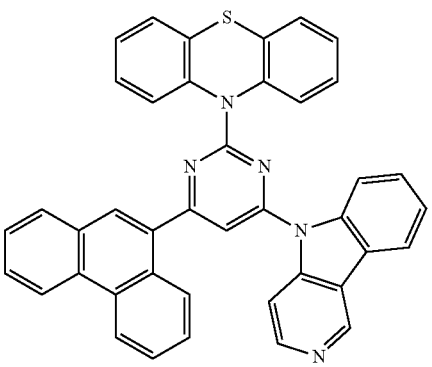

33

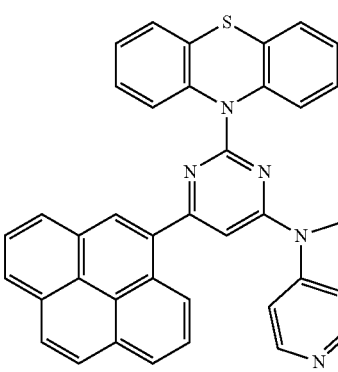

34

According to another aspect of the present invention, an organic light-emitting device includes a first electrode, a second electrode, and an organic layer between the first electrode and the second electrode. The organic layer includes the compound of Formula 1 described above.

The organic layer may include at least one layer selected from a hole injection layer, a hole transport layer, a functional layer having both hole injection and hole transport capabilities (hereinafter, "H-functional layer"), a buffer layer, an electron blocking layer, an emission layer, a hole blocking layer, an electron transport layer, an electron injection layer, and a functional layer having both electron injection and electron transport capabilities (hereinafter, "E-functional layer").

In some embodiments, the organic layer may be an emission layer, and the compound may be used as a host in a fluorescent or phosphorescent device.

In some embodiments, the organic light-emitting device may include an electron injection layer, an electron transport layer, an emission layer, a hole injection layer, a hole transport layer, or a functional layer having both hole injection and transport capabilities; and the emission layer may include the compound of claim 1 and an anthracene-based compound, an arylamine-based compound, or a styryl-based compound.

In some other embodiments, the organic light-emitting device may include an electron injection layer, an electron transport layer, an emission layer, a hole injection layer, a hole transport layer, or a functional layer having both hole injection and transport capabilities. At least one of a red emission layer, a green emission layer, a blue emission layer, and a white emission layer of the emission layer may include a phosphorescent compound. At least one of the hole injection layer, the hole transport layer, and the functional layer having both hole injection and hole transport capabilities may include a charge-generating material. In some embodiments, the charge-generating material may be a p-dopant, and the p-dopant may be a quinone derivative, a metal oxide or a cyano group-containing compound.

In some embodiments, the organic layer may include an electron transport layer, and the electron transport layer may include an electron-transporting organic compound and a metal complex. The metal complex may be a lithium (Li) complex.

The term "organic layer," as used herein, refers to a single layer and/or a plurality of layers disposed between the first and second electrodes of the organic light-emitting device.

The organic layer may include an emission layer, and the emission layer may include the compound of Formula 1 described above. The organic layer may include at least one of a hole injection layer, a hole transport layer, and a functional layer having both hole injection and hole transport capabilities (hereinafter, "H-functional layer"). At least one of the hole injection layer, the hole transport layer, and the functional layer having both hole injection and hole transport capabilities may include the compound of Formula 1.

The compound of Formula 1 in the EML may serve as a phosphorescent host. For example, the compound of Formula 1 may serve as a green phosphorescent host, emitting green light. The compound of Formula 1 in the EML may serve as a fluorescent or phosphorescent dopant, emitting red light, green light, or blue light.

FIG. 1 is a schematic sectional view of an organic light-emitting device according to an embodiment of the present invention. Hereinafter, a structure of an organic light-emitting device according to an embodiment of the present invention and a method of manufacturing the same will be described with reference to FIG. 1.

A substrate (not shown) may be any substrate conventionally used in organic light emitting devices. In some embodiments, the substrate may be a glass substrate or a transparent plastic substrate having good mechanical strength, thermal stability, transparency, surface smoothness, ease of handling, and water resistance.

The first electrode may be formed by depositing or sputtering a first electrode-forming material on the substrate. When the first electrode constitutes an anode, a material having a high work function may be used as the first electrode-forming material to facilitate hole injection. The first electrode may be a reflective electrode or a transmissive electrode. Suitable first electrode-forming materials include transparent and conductive materials such as ITO, IZO, SnO$_2$, and ZnO. The first electrode may be formed as a reflective electrode using magnesium (Mg), aluminum (Al), aluminum-lithium (Al—Li), calcium (Ca), magnesium-indium (Mg—In), magnesium-silver (Mg—Ag), or the like.

The first electrode may have a single-layer structure or a multi-layered structure including at least two layers. For example, the first electrode may have a three-layered structure of ITO/Ag/ITO, but is not limited thereto.

An organic layer(s) is formed on the first electrode.

The organic layer may include a hole injection layer (HIL), a hole transport layer (HTL), a buffer layer (not shown), an emission layer (EML), an electron transport layer (ETL), or an electron injection layer (EIL).

The HIL may be formed on the first electrode 13 by vacuum deposition, spin coating, casting, Langmuir-Blodgett (LB) deposition, or the like.

When the HIL is formed using vacuum deposition, the deposition conditions may vary according to the compound that is used to form the HIL, and the desired structure and thermal properties of the HIL to be formed. For example, the vacuum deposition may be performed at a temperature of about 100° C. to about 500° C., a pressure of about $10^{-8}$ torr to about $10^{-3}$ torr, and a deposition rate of about 0.01 to about 100 Å/sec. However, the deposition conditions are not limited thereto.

When the HIL is formed using spin coating, the coating conditions may vary according to the compound that is used to form the HIL, and the desired structure and thermal properties of the HIL to be formed. For example, the coating rate may be in the range of about 2000 rpm to about 5000 rpm, and the temperature at which heat treatment is performed to remove solvent after coating may be in the range of about 80° C. to about 200° C. However, the coating conditions are not limited thereto.

The HIL may be formed of any material that is commonly used to form a HIL. Examples of the material that can be used to form the HIL include, but not limited to, N,N'-diphenyl-N, N'-bis-[4-(phenyl-m-tolyl-amino)-phenyl]-biphenyl-4,4'-diamine, (DNTPD), a phthalocyanine compound such as copperphthalocyanine, 4,4',4"-tris (3-methylphenylphenylamino)triphenylamine (m-MTDATA), N,N'-di(1-naphthyl)-N,N'-diphenylbenzidine (NPB), TDATA, 2T-NATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), and polyaniline)/poly(4-styrenesulfonate (PANI/PSS).

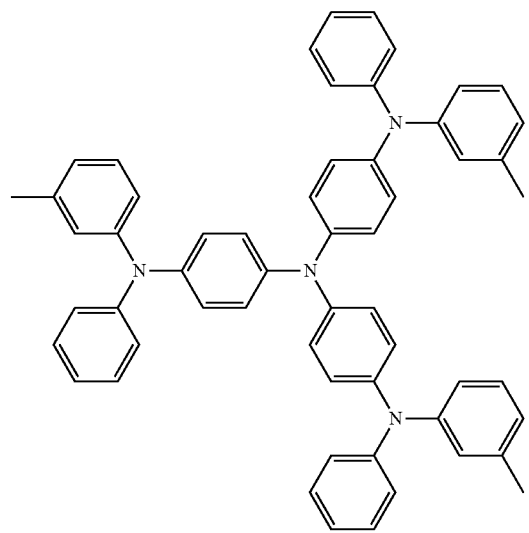

m-MTDATA

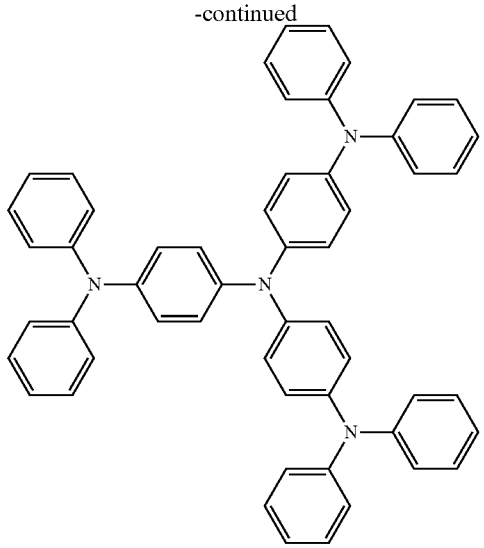

DATA

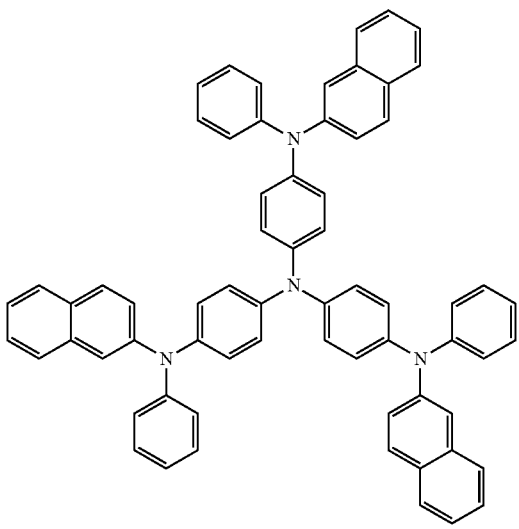

2-TNATA

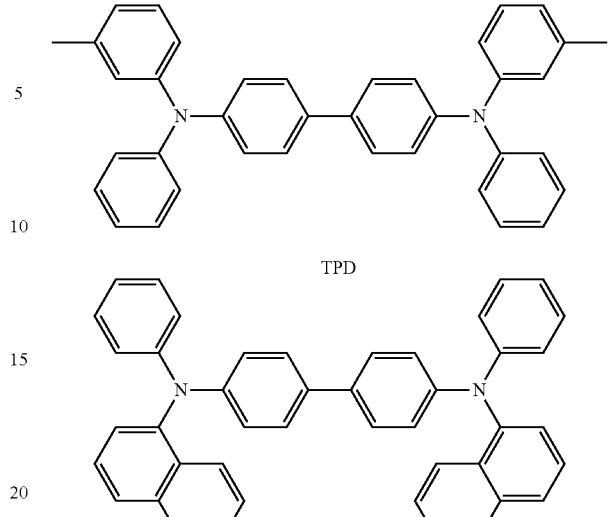

TPD

NPB

The thickness of the HTL may be about 50 Å to about 2,000 Å, and for example, about 100 Å to about 1,500 Å. When the thickness of the HTL is within these ranges, the HTL may have good hole transporting ability without substantially increasing driving voltage.

The H-functional layer (having both hole injection and hole transport capabilities) may contain at least one hole injection layer material and at least one hole transport layer material. The thickness of the H-functional layer may be from about 500 Å to about 10,000 Å, and in some embodiments, may be from about 100 Å to about 1,000 Å. When the thickness of the H-functional layer is within these ranges, the H-functional layer may have good hole injection and transport capabilities without substantially increasing driving voltage.

In some embodiments, at least one of the HIL, HTL, and H-functional layer may include at least one of a compound of Formula 300 below and a compound of Formula 350 below.

Formula 300

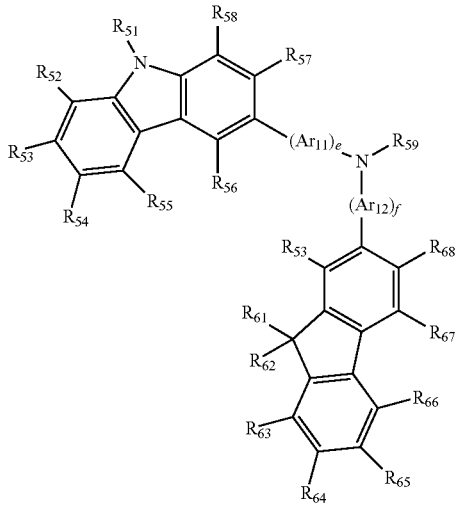

The thickness of the HIL may be about 100 Å to about 10,000 Å, and for example, about 100 Å to about 1,000 Å. When the thickness of the HIL is within these ranges, the HIL may have good hole injecting ability without substantially increasing driving voltage.

Then, a HTL may be formed on the HIL by vacuum deposition, spin coating, casting, Langmuir-Blodgett (LB) deposition, or the like. When the HTL is formed using vacuum deposition or spin coating, the conditions for deposition or coating may be similar to those for the formation of the HIL, though the conditions for the deposition or coating may vary according to the material that is used to form the HTL.

The HTL may be formed of any known material commonly used to form a HTL. Non-limiting examples of suitable hole transport materials include carbazole derivatives, such as N-phenylcarbazole or polyvinylcarbazole, N,N'-bis(3-methylphenyl)-N,N'-diphenyl-[1,1-biphenyl]-4,4'-diamine (TPD), 4,4',4"-tris(N-carbazolyl)triphenylamine (TCTA), and N,N'-di(1-naphthyl)-N,N'-diphenylbenzidine) (NPB).

Formula 350

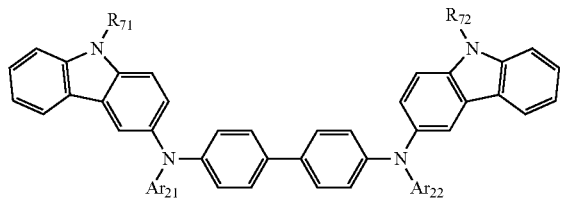

In Formulae 300 and 350, $Ar_{11}$, $Ar_{12}$, $Ar_{21}$ and $Ar_{22}$ may be each independently a substituted or unsubstituted $C_6$-$C_{60}$ arylene group.

In Formula 300, e and f may be each independently an integer from 0 to 5, for example, may be 0, 1, or 2. In a non-limiting embodiment, e may be 1, and f may be 0.

In Formulae 300 and 350, $R_{51}$ to $R_{58}$, $R_{61}$, to $R_{69}$, and $R_{71}$ to $R_{72}$ may be each independently one of a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, or a substituted or unsubstituted $C_6$-$C_{60}$ arylthio group. In some non-limiting embodiments, $R_{51}$ to $R_{58}$, $R_{61}$ to $R_{69}$, $R_{71}$, and $R_{72}$ may be each independently one of a hydrogen atom; a deuterium atom; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid group or a salt thereof; a $C_1$-$C_{10}$ alkyl group (for example, a methyl group, an ethyl group, a propyl group, a butyl group, a pentyl group, a hexyl group, or the like); a $C_1$-$C_{10}$ alkoxy group (for example, a methoxy group, an ethoxy group, a propoxy group, a butoxy group, a pentoxy group, or the like); a $C_1$-$C_{10}$ alkyl group or a $C_1$-$C_{10}$ alkoxy group substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, or a phosphoric acid group or a salt thereof; a phenyl group; a naphthyl group; an anthryl group; a fluorenyl group; a pyrenyl group; or a phenyl group, a naphthyl group, an anthryl group, a fluorenyl group, or a pyrenyl group substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, or a $C_1$-$C_{10}$ alkoxy group.

In Formula 300, $R_{59}$ may be independently a phenyl group, a naphthyl group, an anthryl group, a biphenyl group, or a pyridyl group; or a phenyl group, a naphthyl group, an anthryl group, a biphenyl group, or a pyridyl group substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a substituted or unsubstituted $C_1$-$C_{20}$ alkyl group, or a substituted or unsubstituted $C_1$-$C_{20}$ alkoxy group.

In an embodiment, the compound of Formula 300 may be a compound represented by Formula 300A below.

Formula 300A

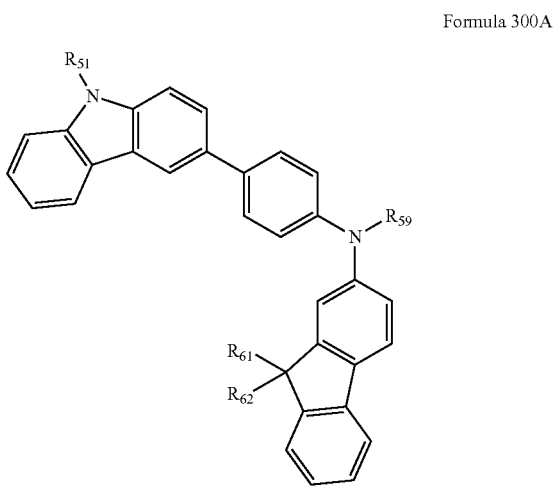

$R_{51}$, $R_{60}$, $R_{61}$ and $R_{59}$ in Formula 300A are as defined above, and thus a detailed description thereof will not be provided here.

In some non-limiting embodiments, at least one of the HIL, HTL, and H-functional layer may include at least one of the compounds represented by Formulae 301 to 320 below.

301

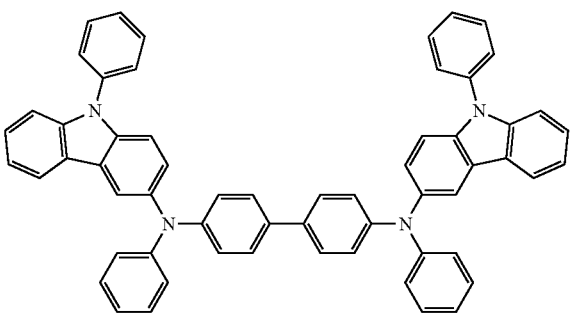

302

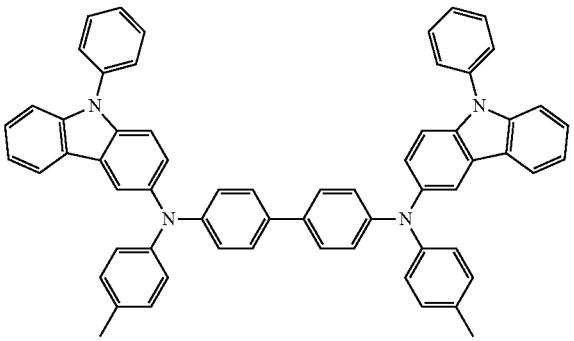

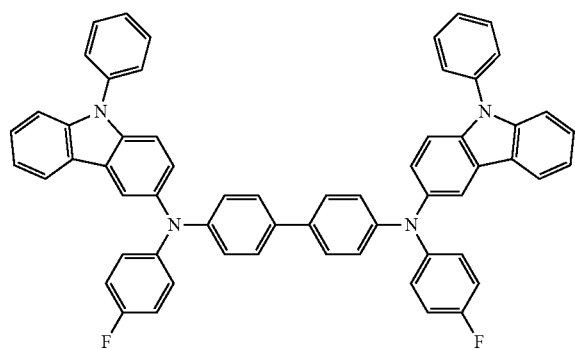
303
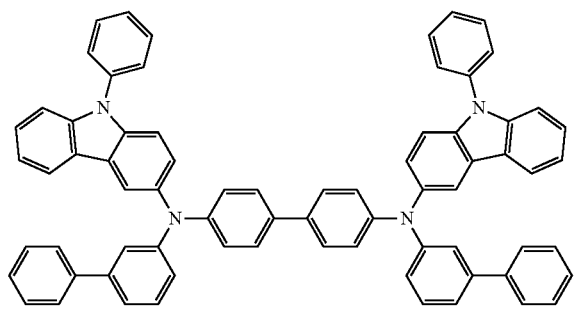
307
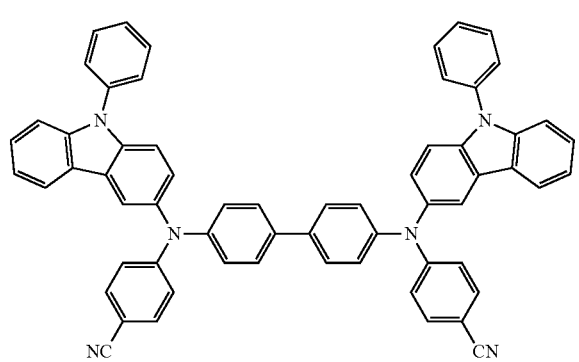
304
308
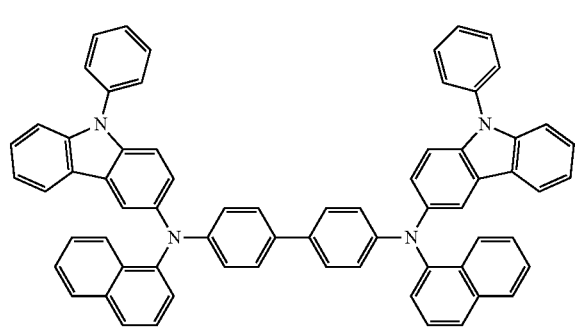
305
306
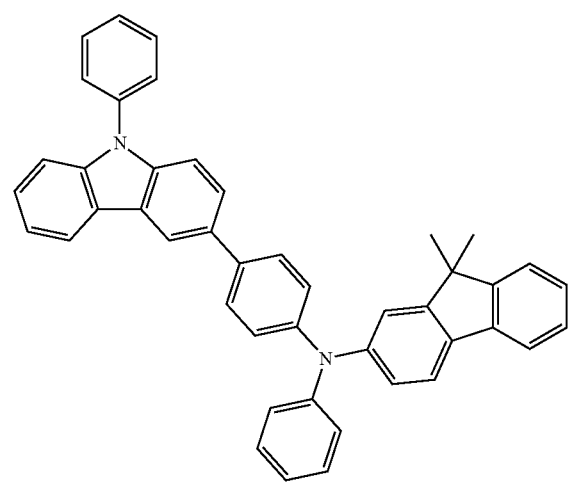
309

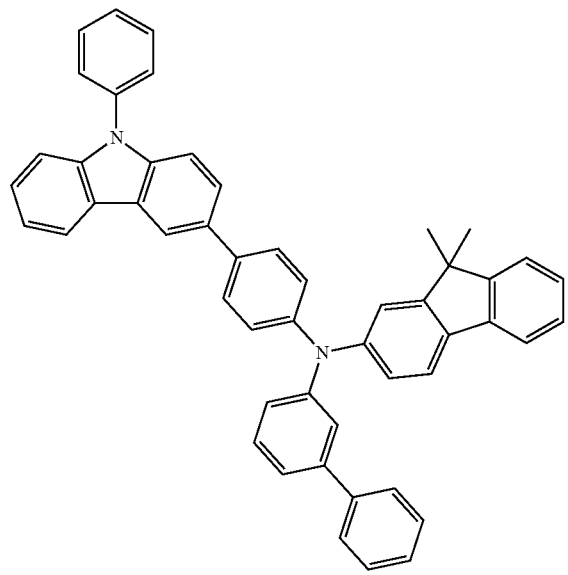
310
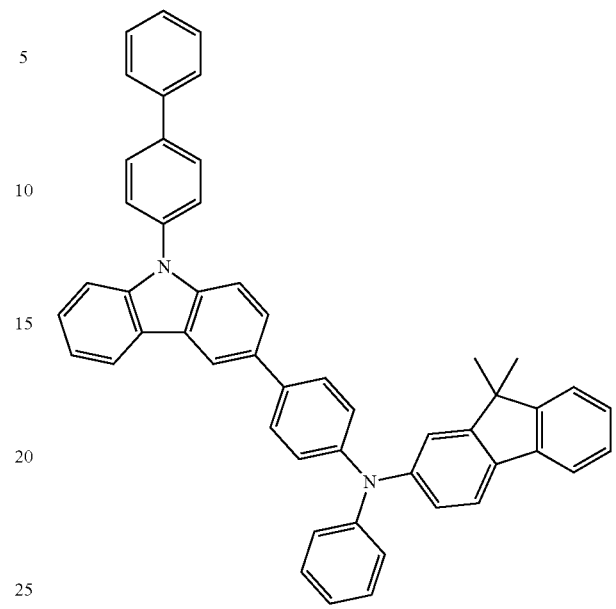
312
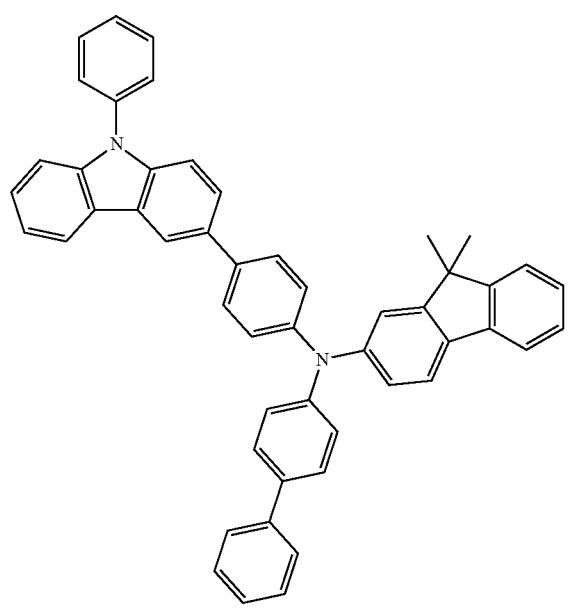
311
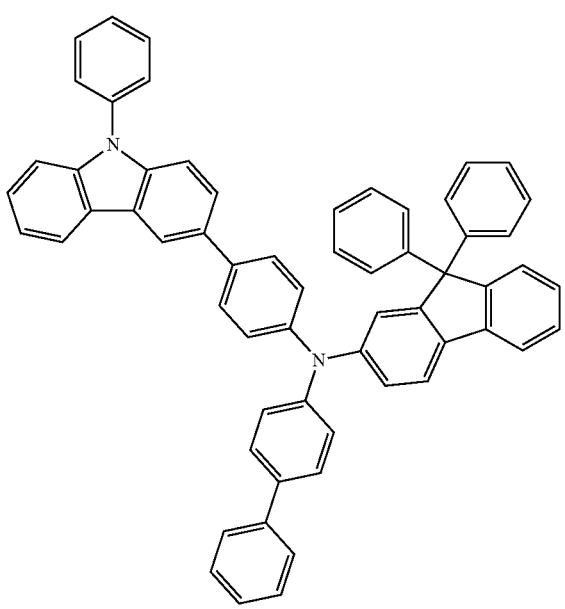
313

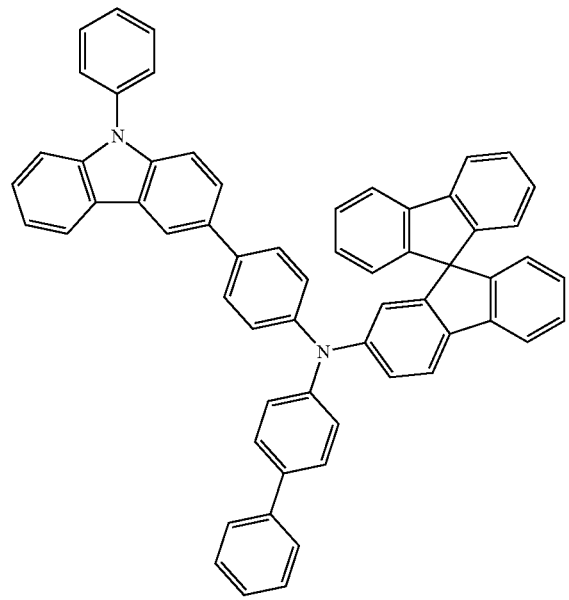
314
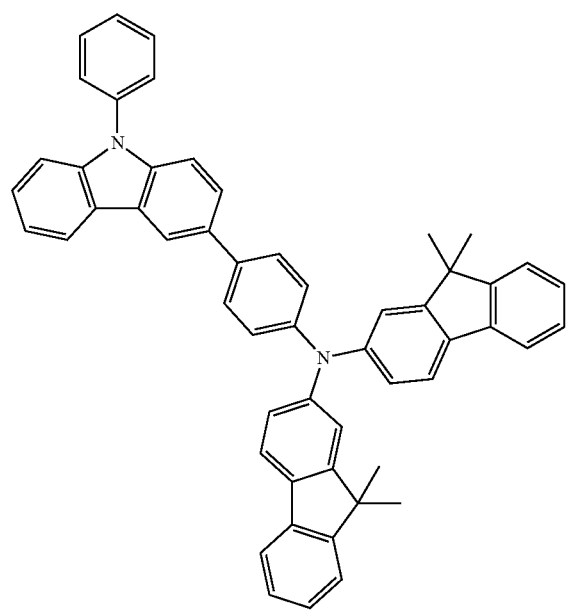
315
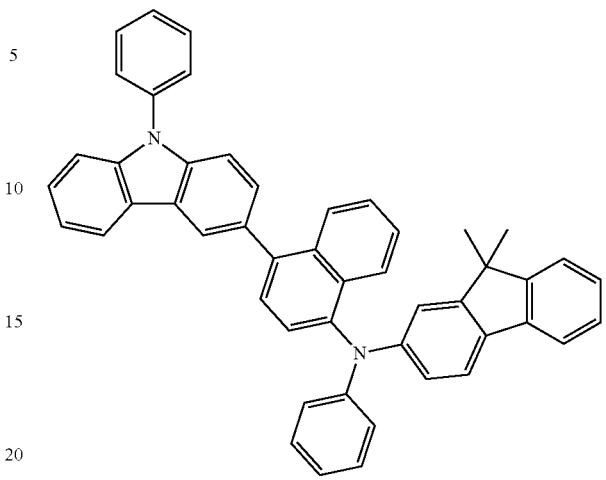
316
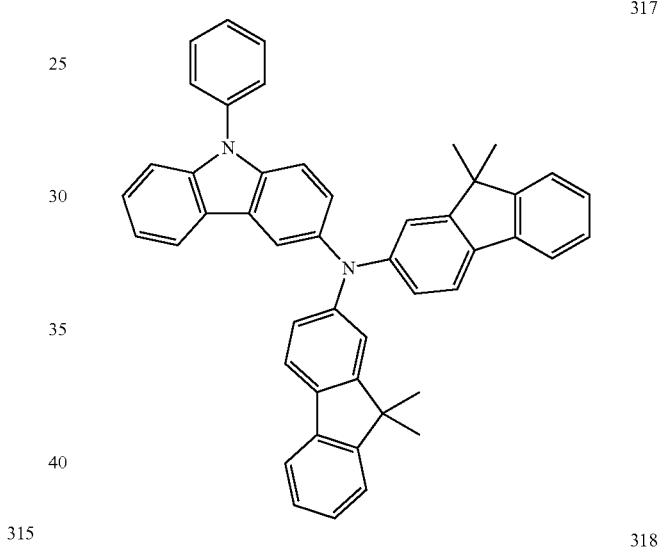
317
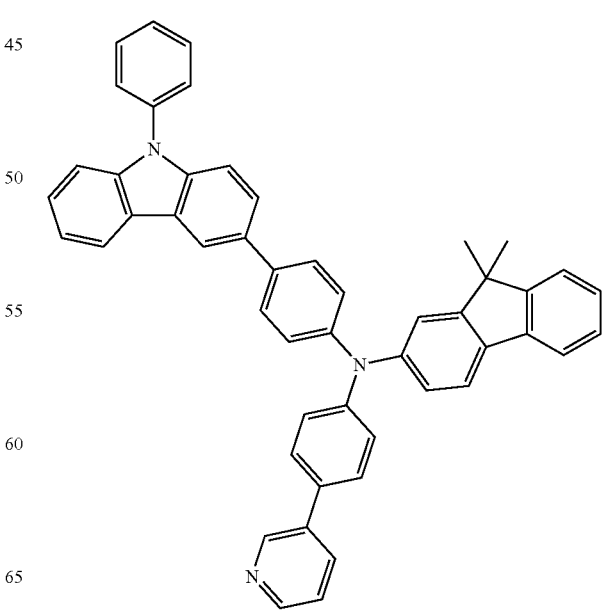
318

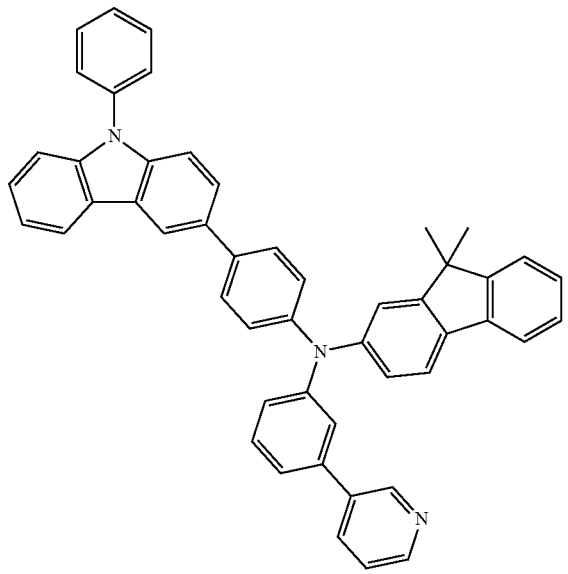

319

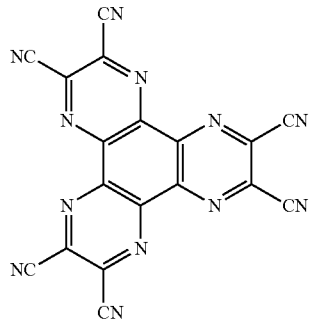

Compound 200

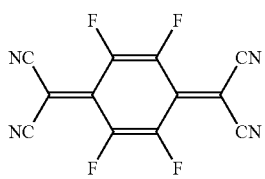

<F4-CTNQ>

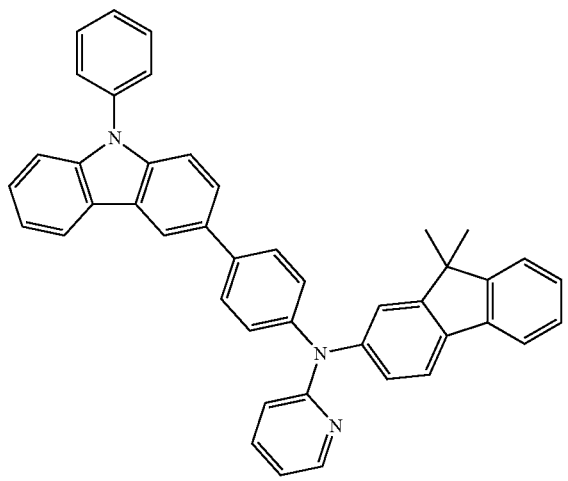

320

At least one of the HIL, HTL, and H-functional layer may further include a charge-generating material for improved layer conductivity, in addition to a hole injecting material, hole transport material, and/or a material having both hole injection and hole transport capabilities, as described above.

The charge-generating material may be, for example, a p-dopant. The p-dopant may be selected from quinone derivatives, metal oxides, and compounds with a cyano group, but is not limited thereto. Non-limiting examples of the p-dopant include quinone derivatives such as tetracyanoquinonedimethane (TCNQ), 2,3,5,6-tetrafluoro-tetracyano-1,4-benzoquinonedimethane (F4-CTNQ), and the like; metal oxides such as tungsten oxide, molybdenum oxide, and the like; and cyano-containing compounds such as Compound 200 below.

When the hole injection layer, hole transport layer, or H-functional layer further includes a charge-generating material, the charge-generating material may be homogeneously dispersed or inhomogeneously distributed in the layer.

A buffer layer may be disposed between at least one of the HIL, HTL, and H-functional layer, and the EML. The buffer layer may compensate for an optical resonance distance of light according to a wavelength of the light emitted from the EML, and thus may increase efficiency. The butter layer may include any known hole injecting material or hole transporting material. In some other embodiments, the buffer layer may include the same material as one of the materials included in the HIL, HTL, or H-functional layer that underlie the buffer layer.

Then, an EML may be formed on the HTL, H-functional layer, or buffer layer by vacuum deposition, spin coating, casting, Langmuir-Blodget (LB) deposition, or the like. When the EML is formed using vacuum deposition or spin coating, the deposition and coating conditions may be similar to those for the formation of the HIL, though the conditions for deposition and coating may vary according to the material that is used to form the EML.

The EML may include the compound of Formula 1.

The EML may further include a host, in addition to the compound of Formula 1.

Examples of the host are $Alq_3$, 4,4'-N,N'-dicarbazole-biphenyl (CBP), poly(n-vinylcarbazole) (PVK), 9,10-di(naphthalene-2-yl)anthracene (ADN), TCTA, 1,3,5-tris(N-phenyl-benzimidazole-2-yl)benzene (TPBI), 3-tert-butyl-9,10-di-2-naphthylanthracene (TBADN), E3, distyrylarylene (DSA), dmCBP (see formula below), and Compounds 501 to 509 below, but are not limited thereto.

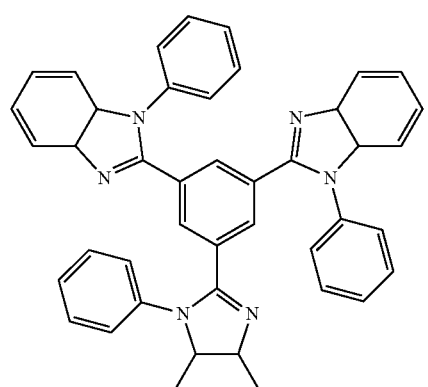
TPBI
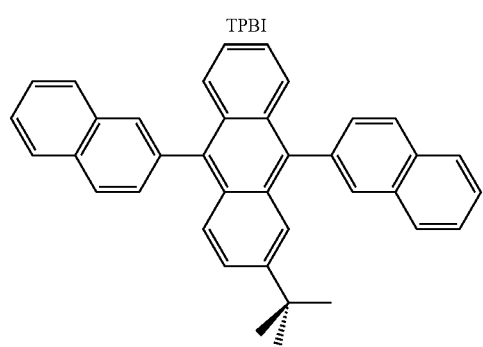
TBADN
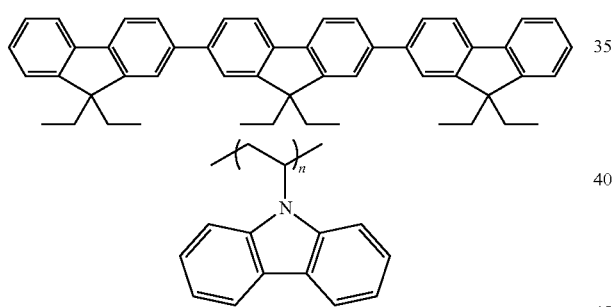
PVK
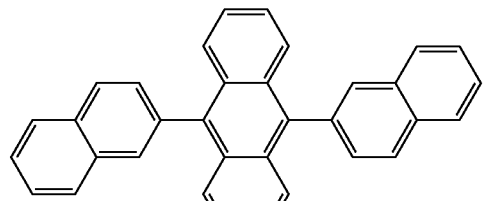
ADN
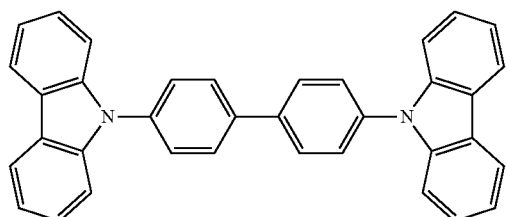
CBP
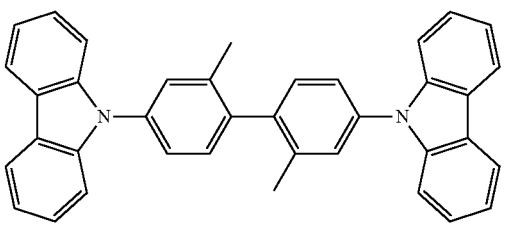
dmCBP
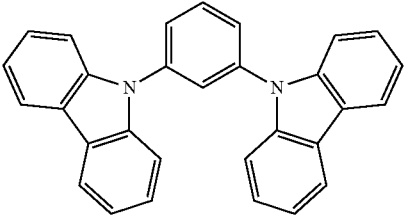
501
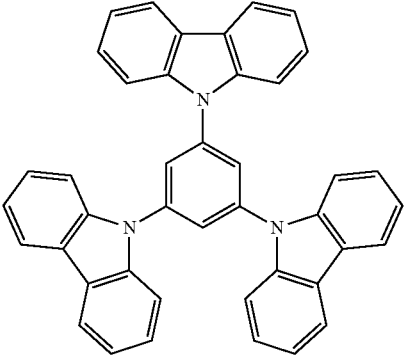
502
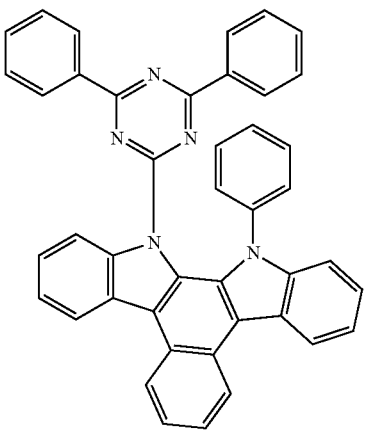
503

504 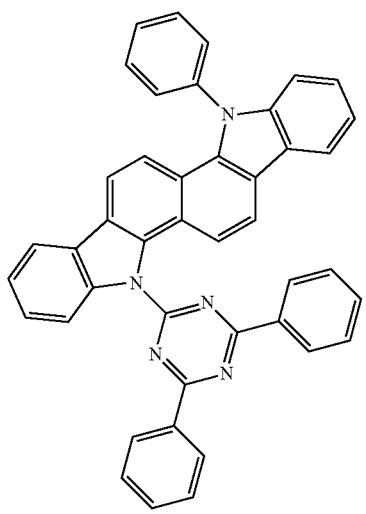

505 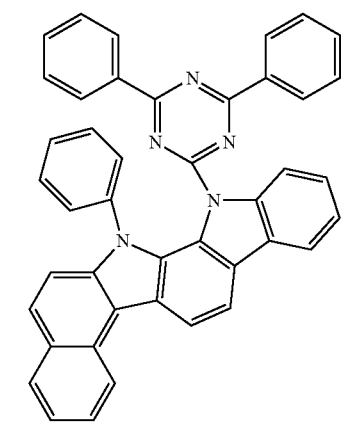

506 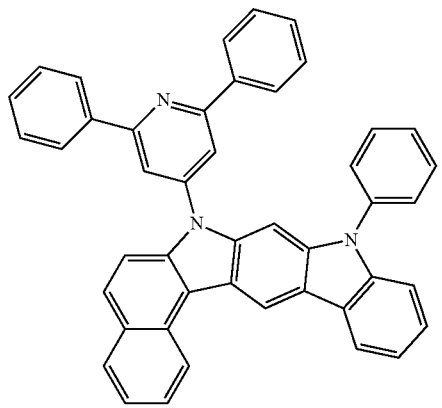

507 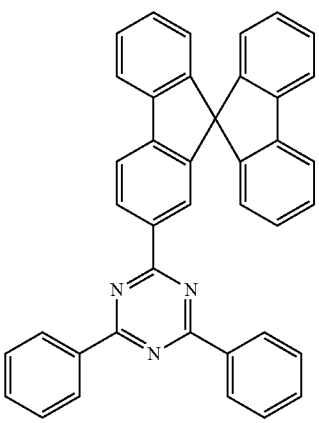

508 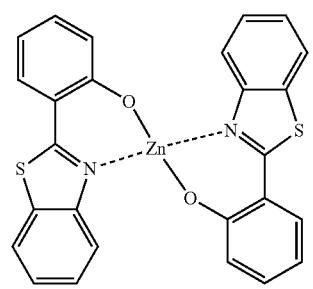

509 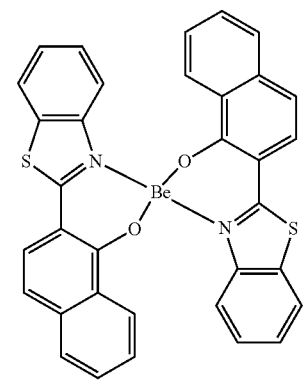

In some embodiments, an anthracene-based compound represented by Formula 400 below may be used as the host.

Formula 400

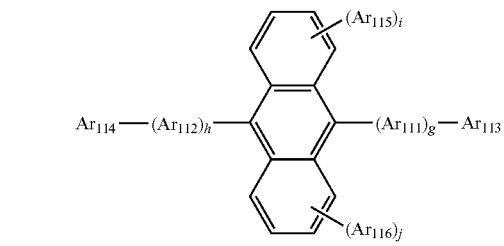

In Formula 400, $Ar_{111}$ and $Ar_{112}$ are each independently a substituted or unsubstituted $C_6$-$C_{60}$ arylene group; $Ar_{113}$ to $Ar_{116}$ are each independently a substituted or unsubstituted $C_1$-$C_{10}$ alkyl group or a substituted or unsubstituted $C_6$-$C_{60}$ aryl group; and g, h, l, and j are each independently an integer from 0 to 4.

In some non-limiting embodiments, $Ar_{111}$ and $Ar_{112}$ in Formula 400 may be each independently a phenylene group, a naphthylene group, a phenanthrenylene group, or a pyrenylene group; or a phenylene group, a naphthylene group, a phenanthrenylene group, a fluorenyl group, or a pyrenylene group substituted with at least one of a phenyl group, a naphthyl group, and an anthryl group.

In Formula 400 above, g, h, l, and j may be each independently 0, 1, or 2.

In some non-limiting embodiments, $Ar_{113}$ to $Ar_{116}$ in Formula 400 may be each independently one of a $C_1$-$C_{10}$ alkyl group substituted with at least one of a phenyl group, a naphthyl group, and an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group, or a fluorenyl group substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, or a fluorenyl group; or

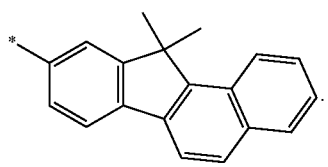 [SMILES: *c1ccc2c(c1)C(C)(C)c1c-2ccc2ccccc12]

For example, the anthracene compound of Formula 400 above may be one of the compounds represented by the following formulae, but is not limited thereto:

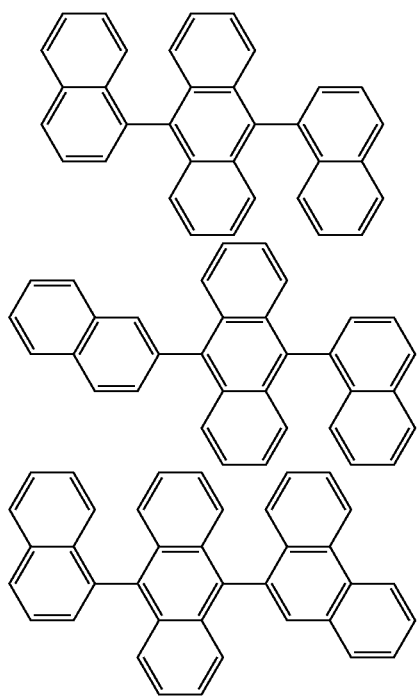

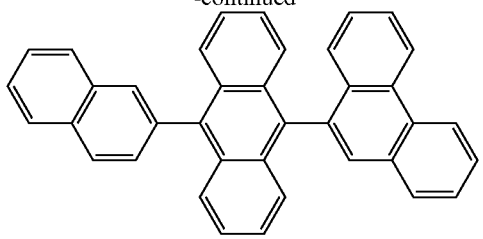

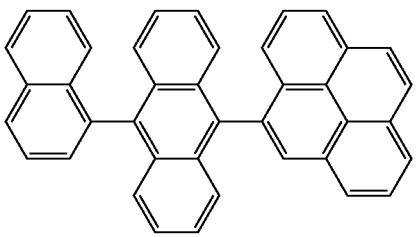

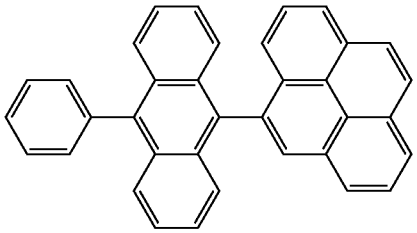

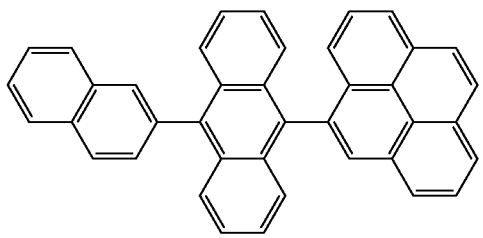

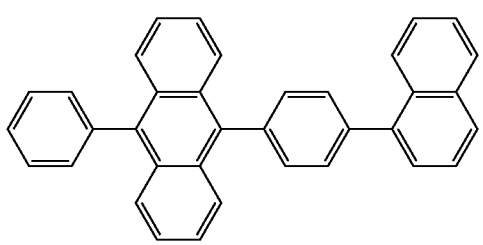

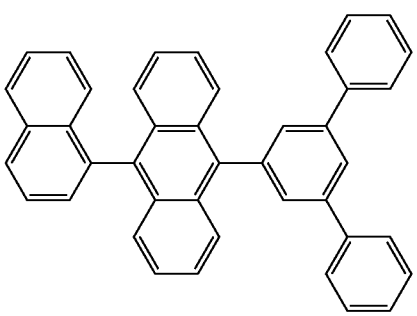

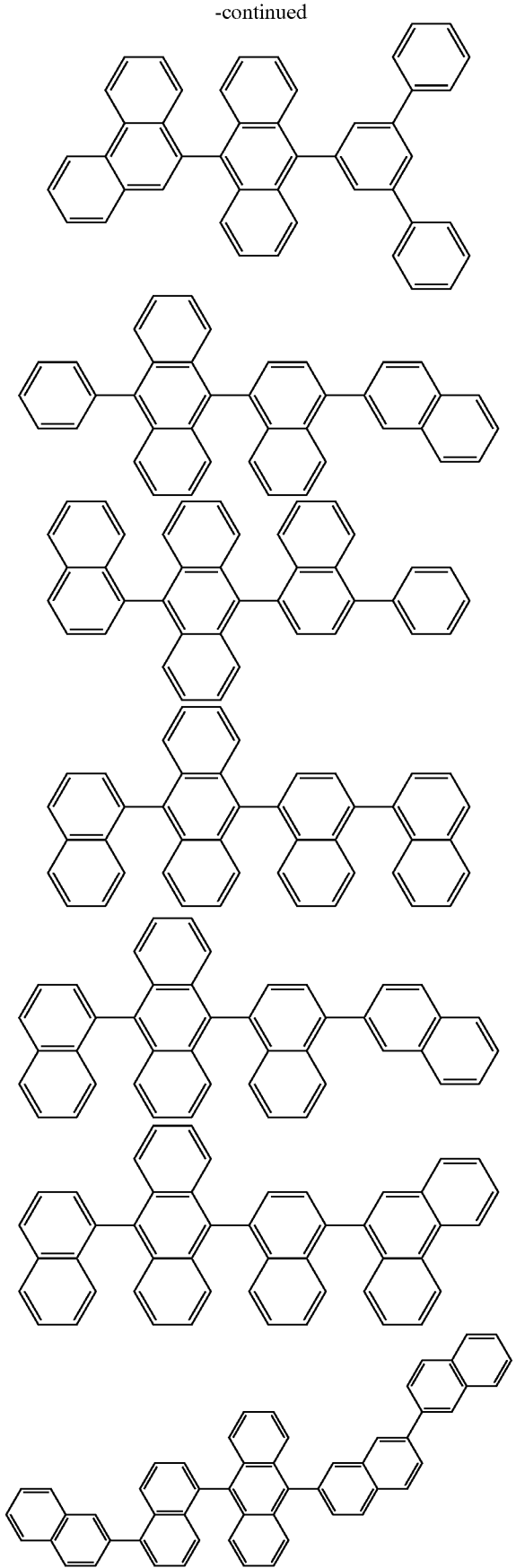

-continued
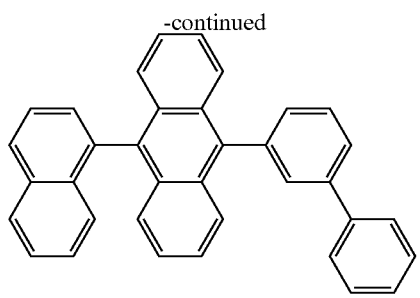
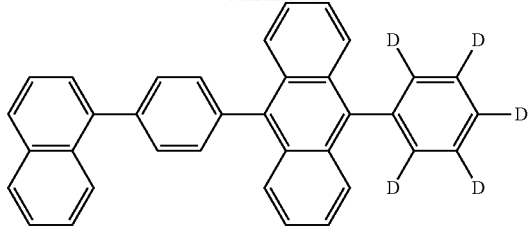
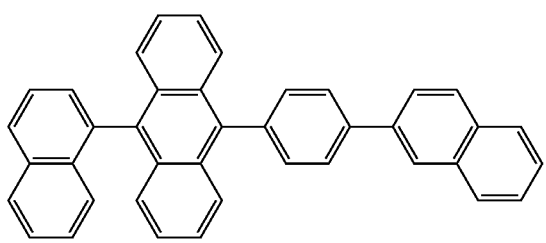
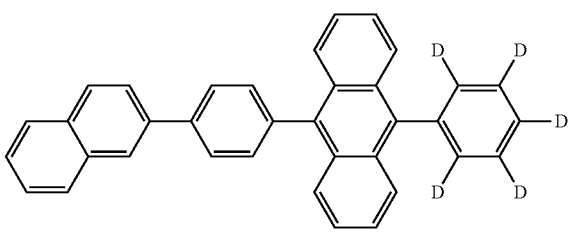
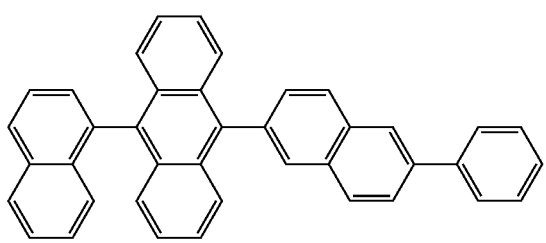
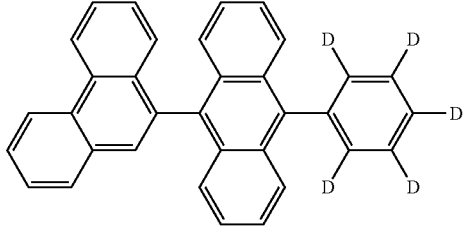
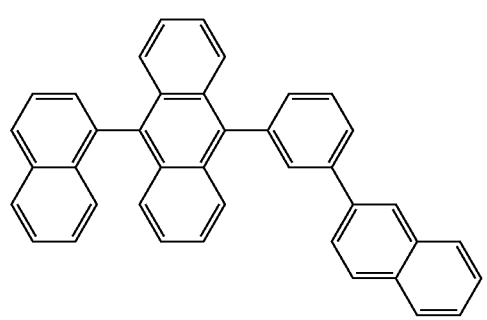
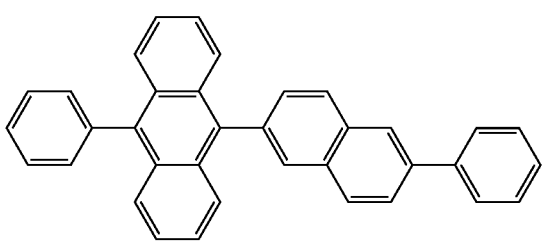
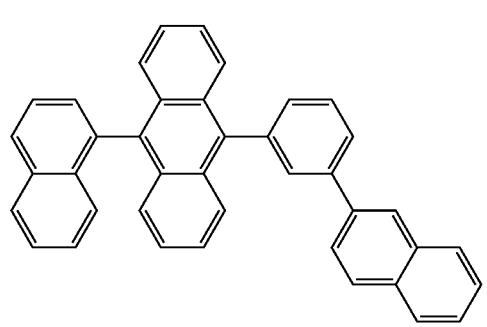
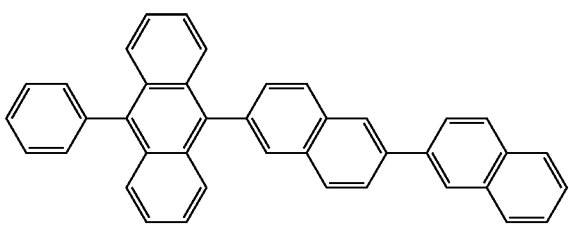
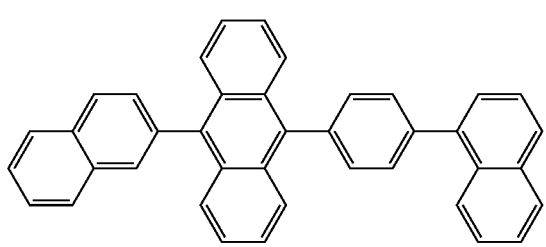
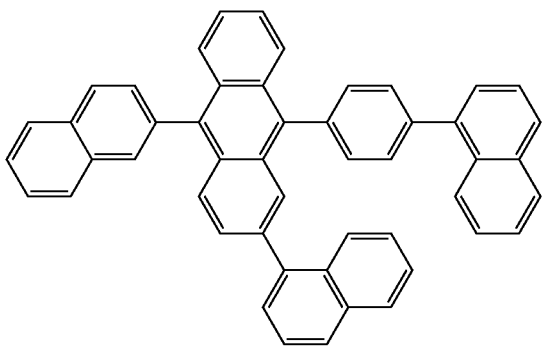

-continued
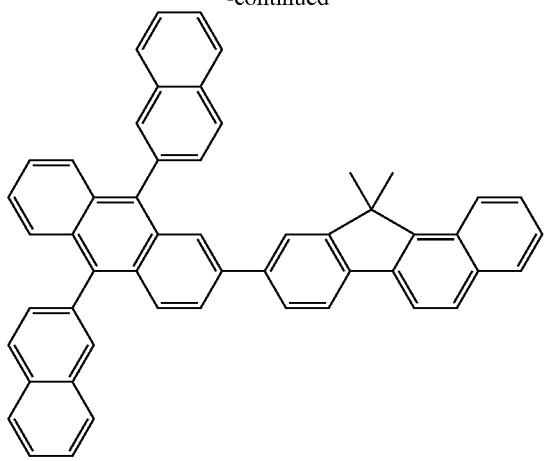
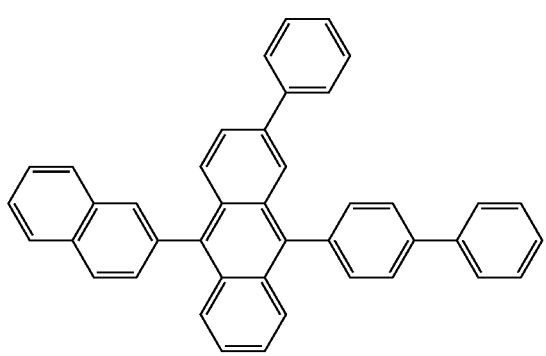
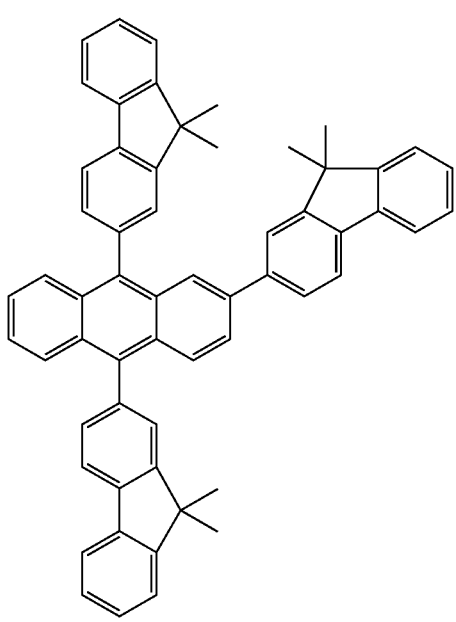
-continued
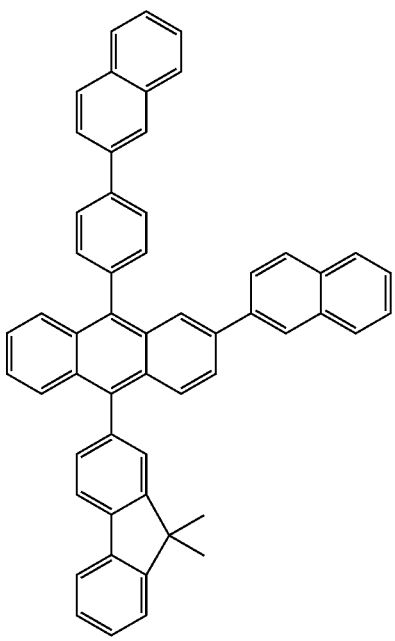
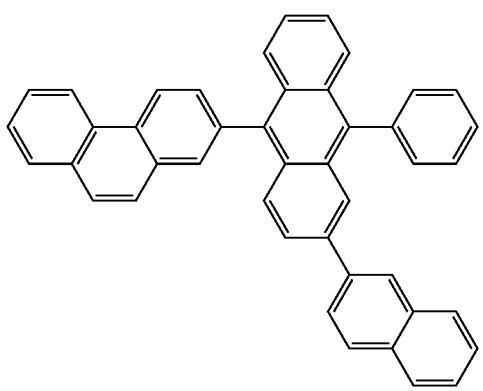 [SMILES: c1ccc(-c2c3ccccc3c(-c3ccc4c(ccc5ccccc54)c3)c3ccc(-c4ccc5ccccc5c4)cc23)cc1]
In some embodiments, an anthracene-based compound represented by Formula 401 below may be used as the host.
Formula 401
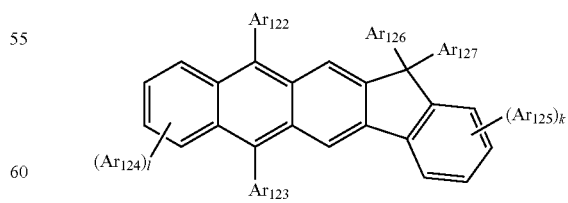
$Ar_{122}$ to $Ar_{125}$ in Formula 401 above may be defined as described above in connection with $Ar_{113}$ of Formula 400, and thus detailed descriptions thereof will not be provided here.

Ar₁₂₆ and Ar₁₂₇ in Formula 401 above may be each independently a $C_1$-$C_{10}$ alkyl group, for example, a methyl group, an ethyl group, or a propyl group.

In Formula 401, k and l may be each independently an integer from 0 to 4, for example, 0, 1, or 2.

For example, the anthracene compound of Formula 401 above may be one of the compounds represented by the following formulae, but is not limited thereto:

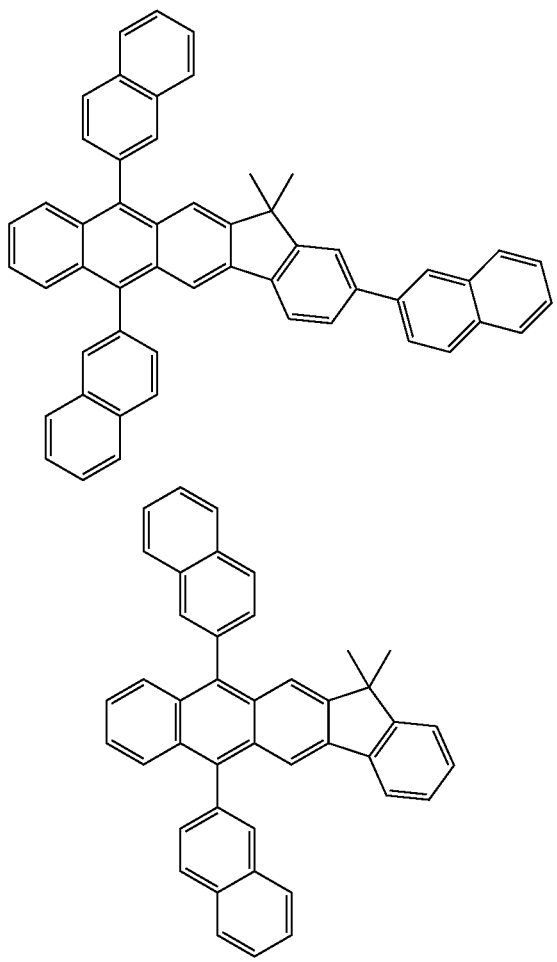

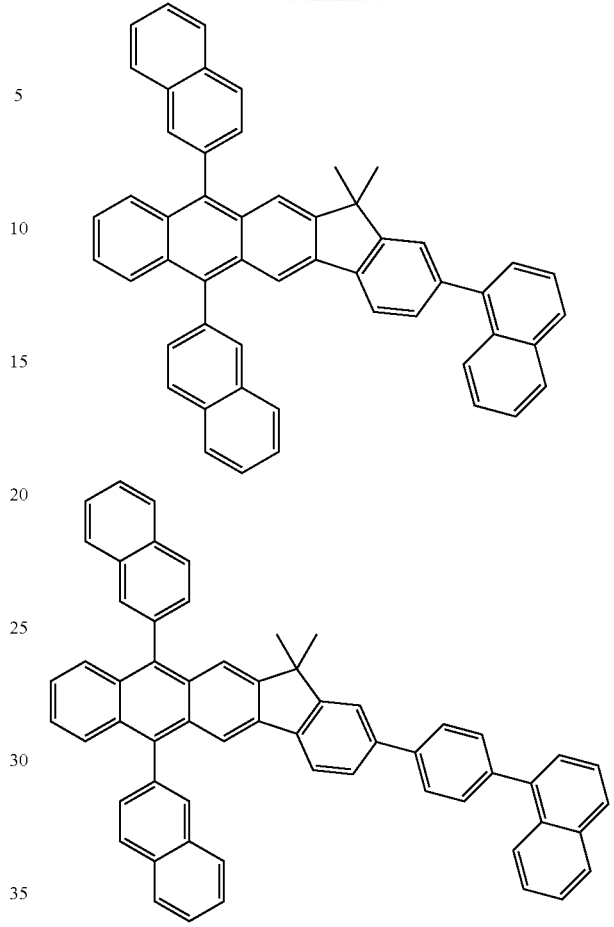

When the organic light-emitting device is a full color organic light-emitting device, the emission layer may be patterned into a red emission layer, a green emission layer, and a blue emission layer. The EML may further include the compound of Formula 1 as a green phosphorescent host.

At least one of the red EML, the green EML, and the blue EML may include a dopant, as described below (ppy=phenylpyridine).

Non-limiting examples of the blue dopant include compounds represented by the following formulae.

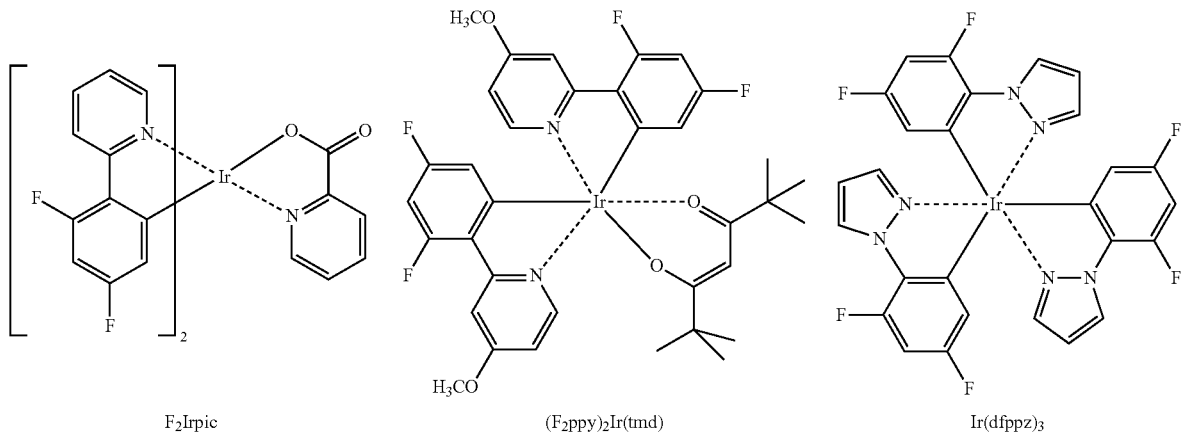

-continued
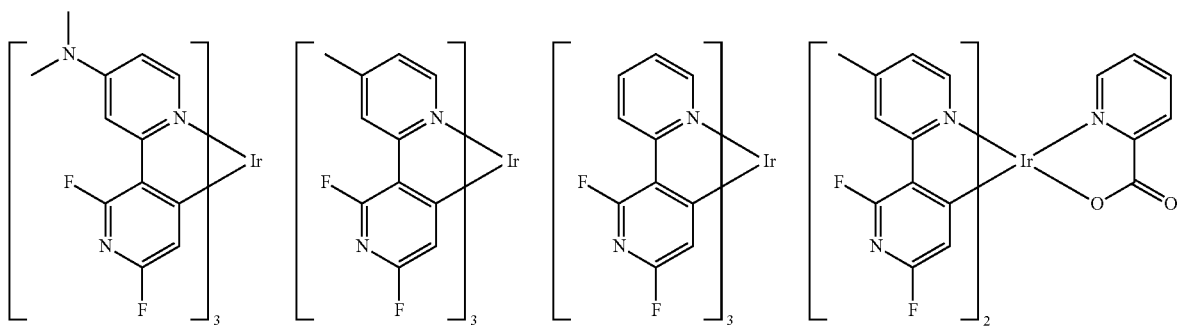
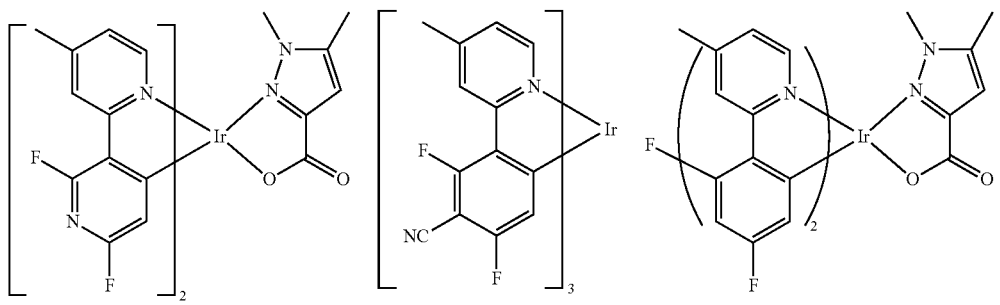
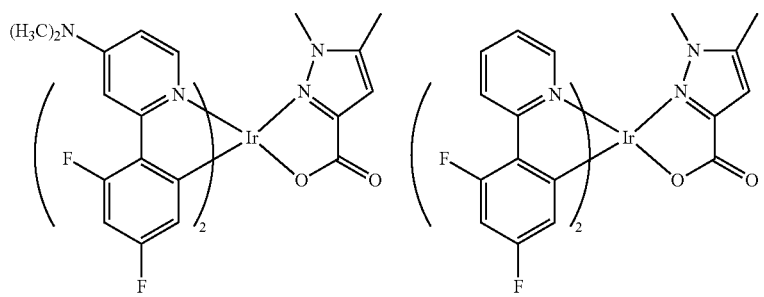
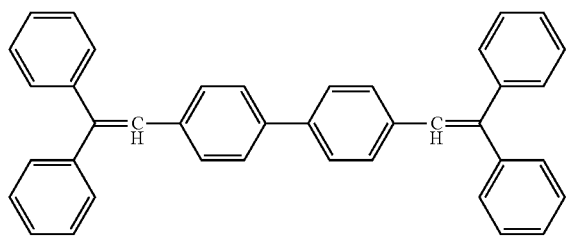
DPVBi
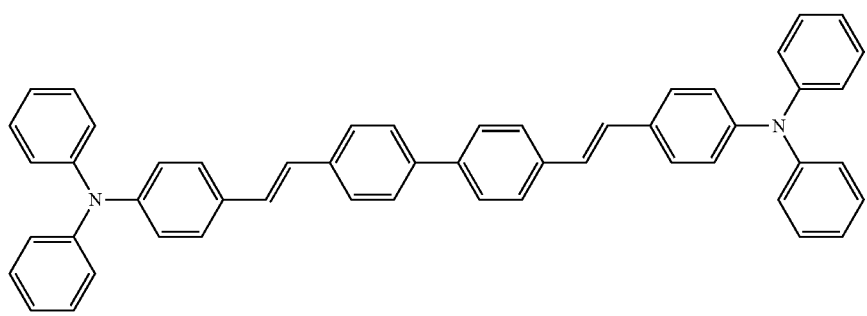
DPAVBi

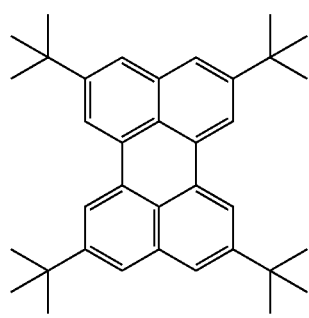
TBPe
Non-limiting examples of the red dopant include compounds represented by the following formulae.
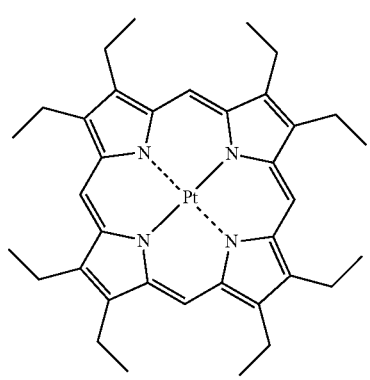
PtOEP
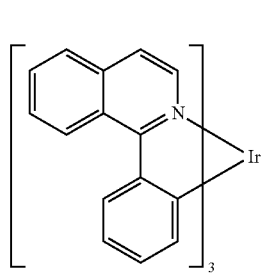
Ir(piq)₃
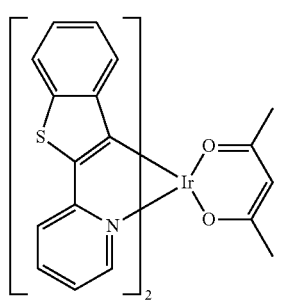
Btp₂Ir(acac)
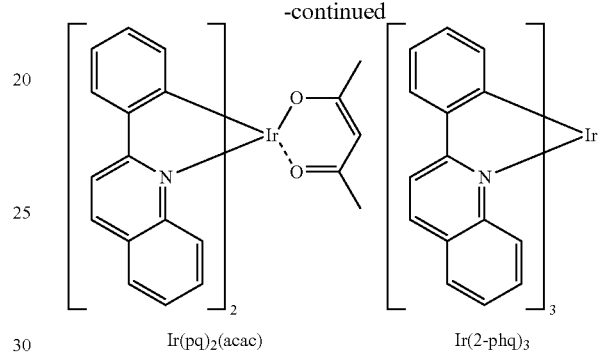
Ir(pq)₂(acac)    Ir(2-phq)₃
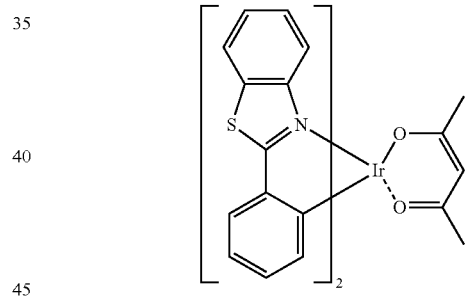
Ir(BT)₂(acac)
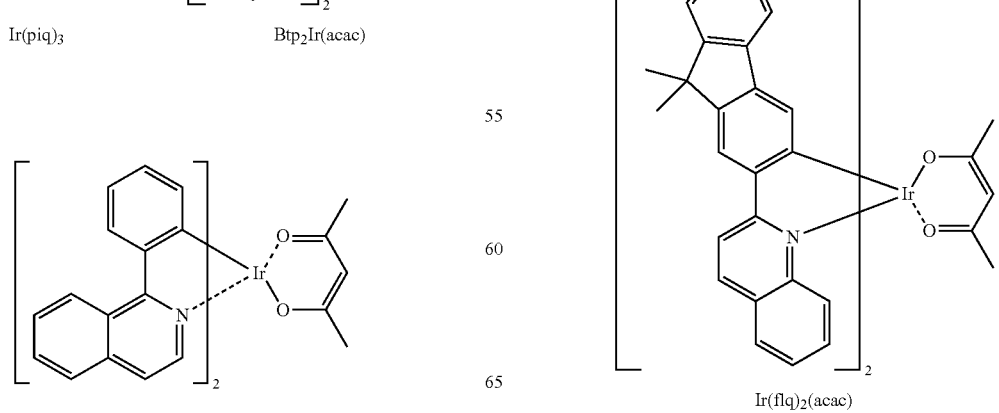
Ir(flq)₂(acac)

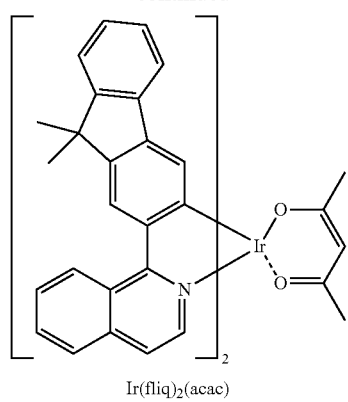
Ir(fliq)₂(acac)
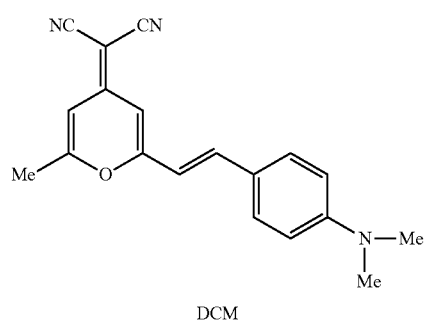
DCM
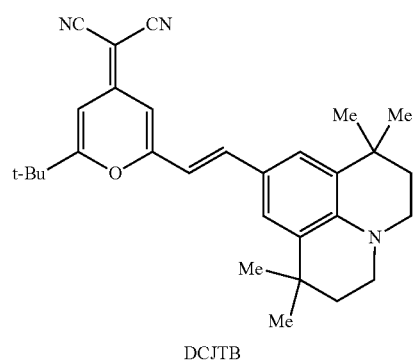
DCJTB
Non-limiting examples of the green dopant include compounds represented by the following formulae.
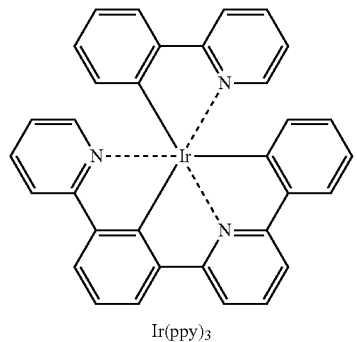
Ir(ppy)₃
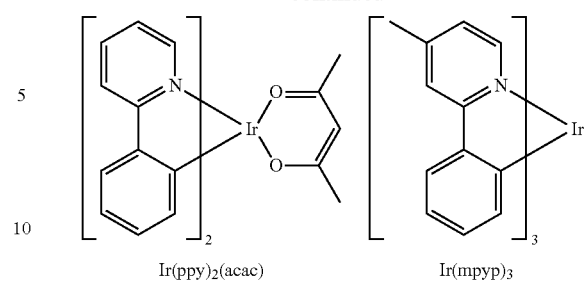
Ir(ppy)₂(acac)    Ir(mpyp)₃
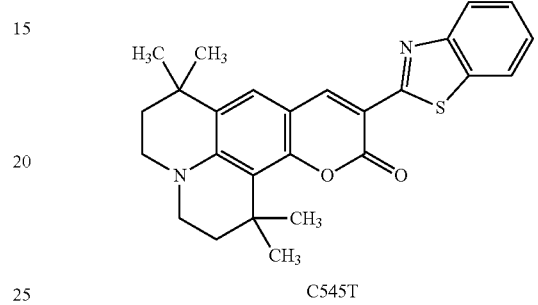
C545T
Non-limiting examples of the dopant that may be used in the EML include Pt complexes represented by the following formulae.
D1
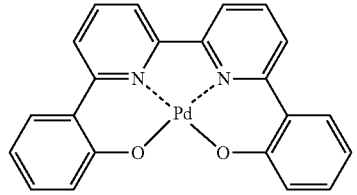
D2
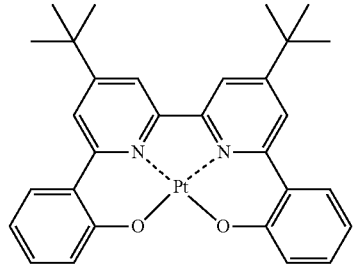
D3
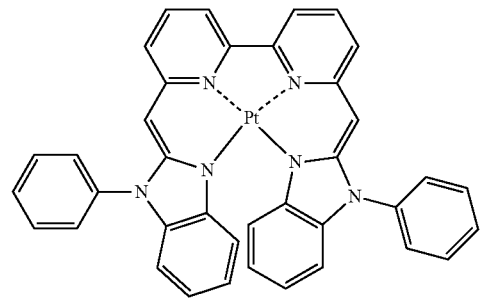

D4
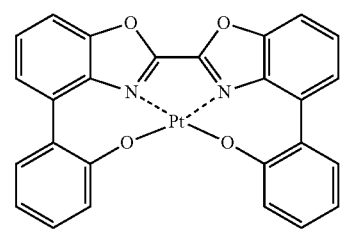
D5
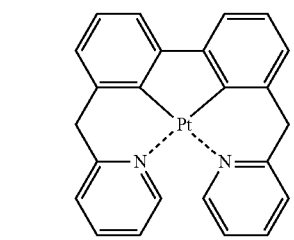
D6
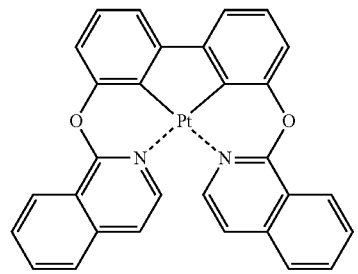
D7
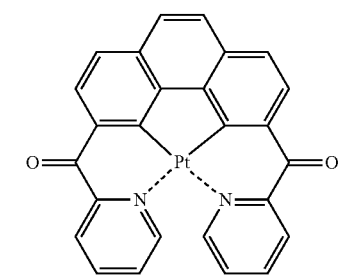
D8
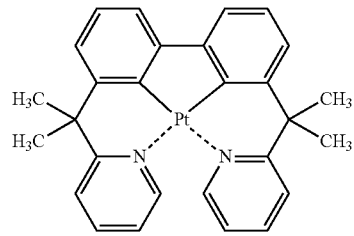
D9
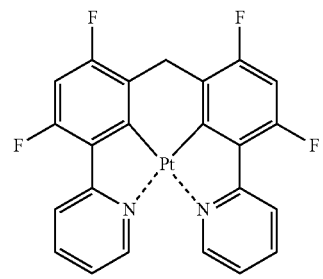
D10
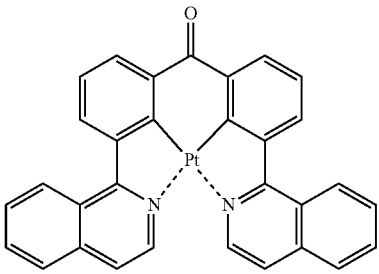
D11
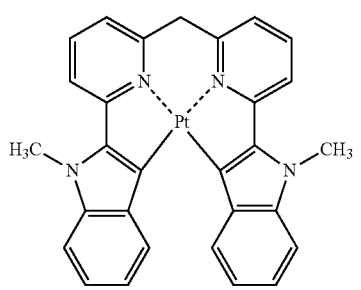
D12
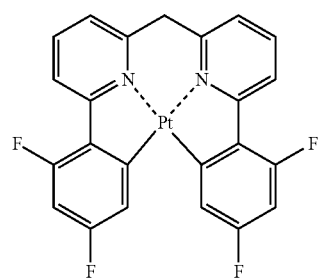
D13
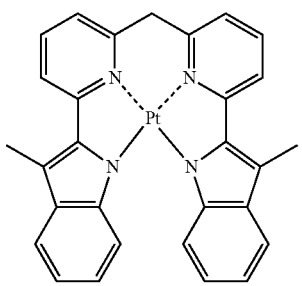
D14
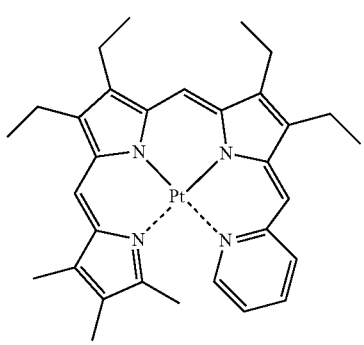

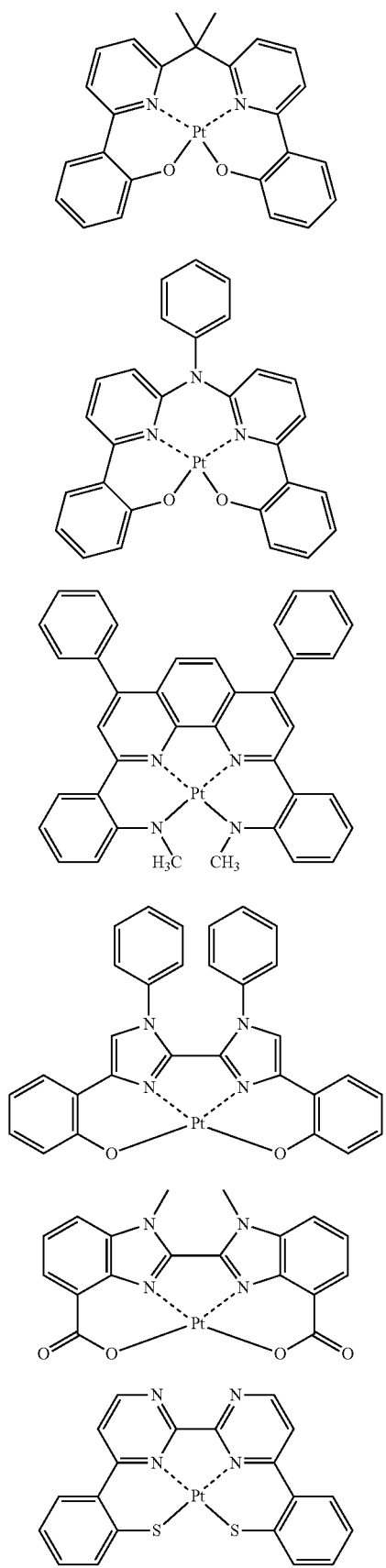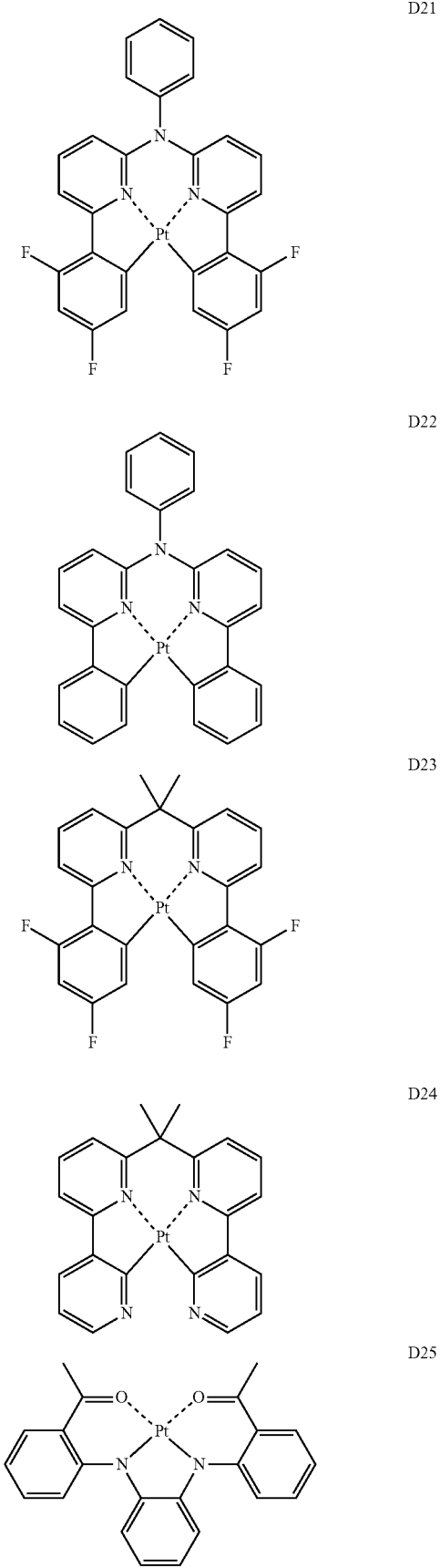

-continued
D26
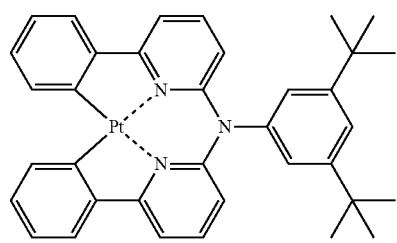
D27
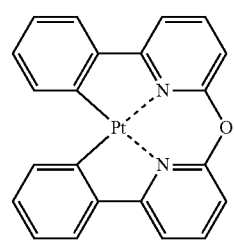
D28
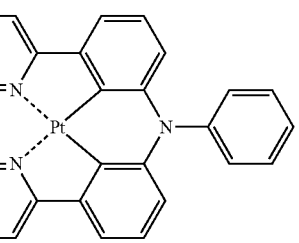
D29
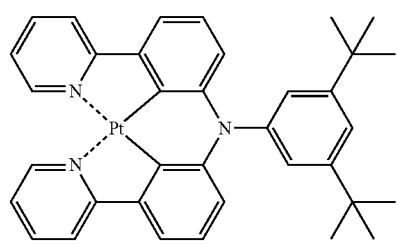
D30
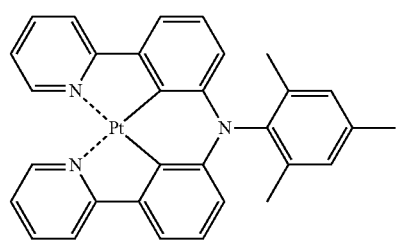
D31
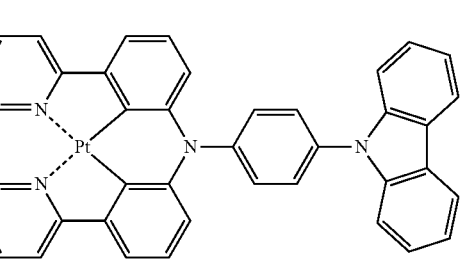
-continued
D32
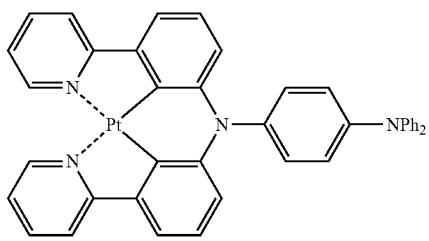
D33
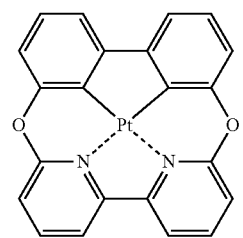
D34
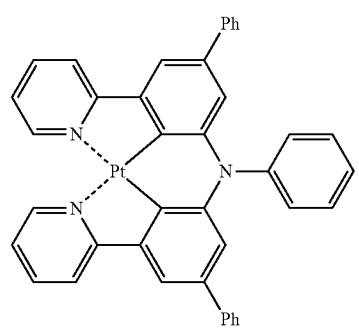
D35
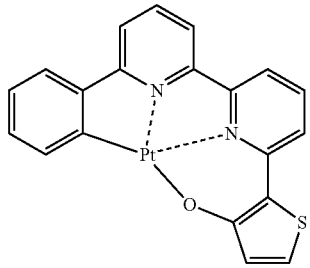
D36
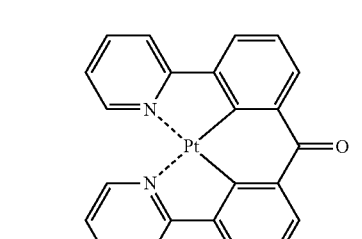

-continued
D37
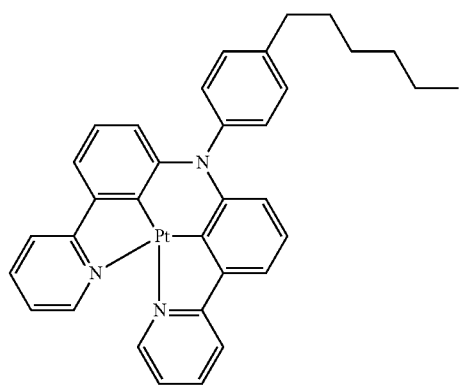
D38
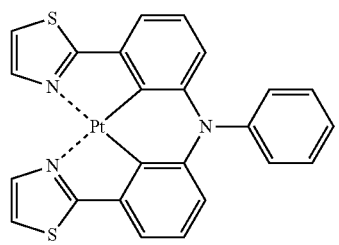
D39
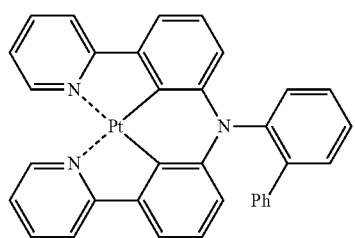
D40
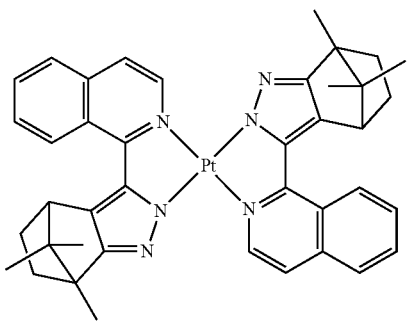
D41
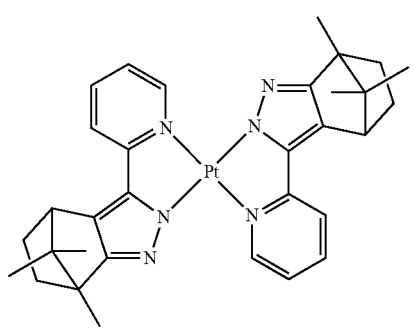
-continued
D42
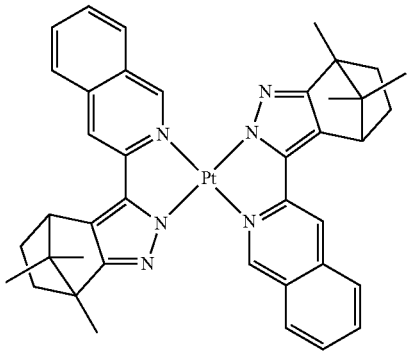
D43
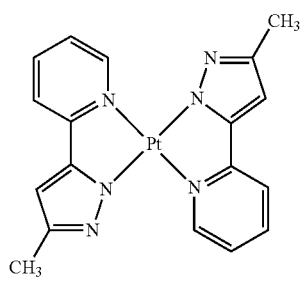
D44
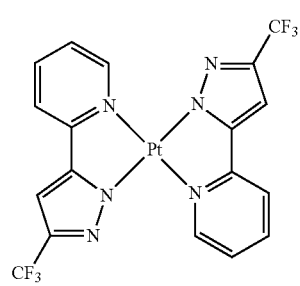
D45
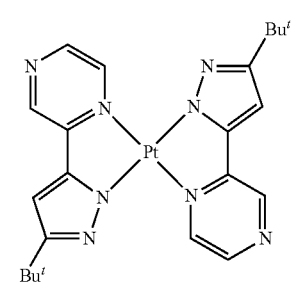
D46
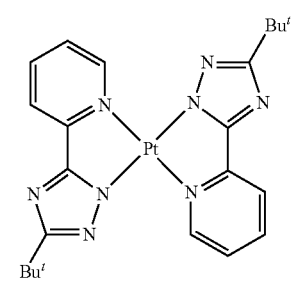

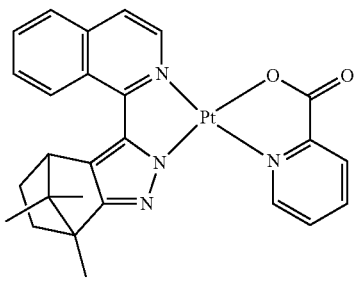

D47

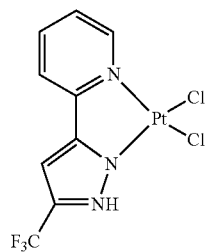

D48

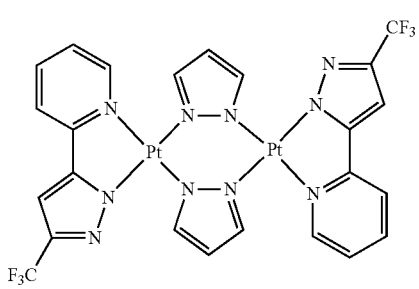

D49

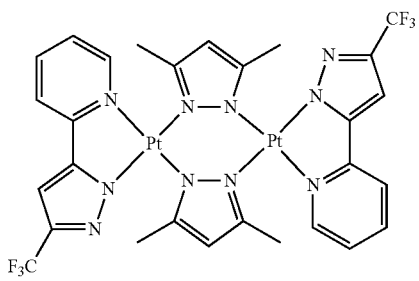

D50

Non-limiting examples of the dopant that may be used in the EML include Os complexes represented by the following formulae.

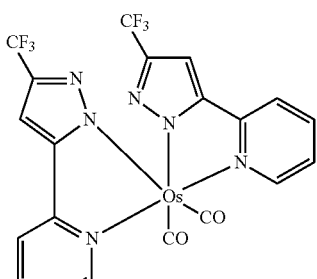

Os(fppz)$_2$(CO)$_2$

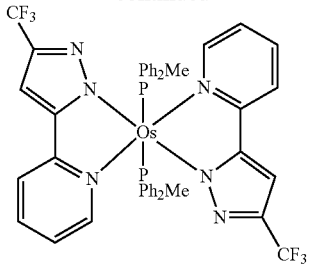

Os(fppz)$_2$(PPh$_2$Me)$_2$

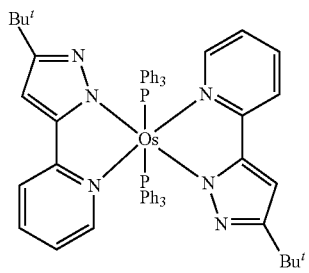

Os(bppz)$_2$(PPh$_3$)$_2$

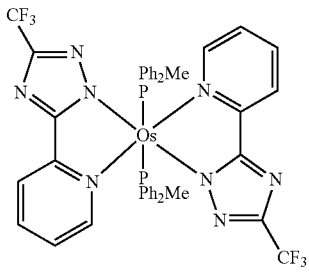

Os(fptz)$_2$(PPh$_2$Me)$_2$

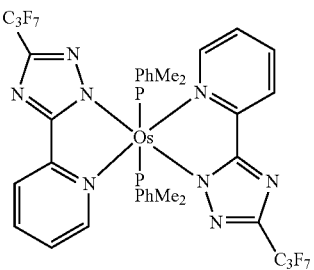

Os(hptz)$_2$(PPhMe$_2$)$_2$

When the EML includes both a host and a dopant, the amount of the dopant may be from about 0.01 to about 15 parts by weight based on 100 parts by weight of the host. However, the amount of the dopant is not limited to this range.

The thickness of the EML may be about 100 Å to about 1000 Å, for example, about 200 Å to about 600 Å. When the thickness of the EML is within these ranges, the EML may have good light emitting ability without substantially increasing driving voltage.

Then, an ETL may be formed on the EML by vacuum deposition, spin coating, casting, or the like. When the ETL is formed using vacuum deposition or spin coating, the deposition or coating conditions may be similar to those for the formation of the HIL, though the deposition or coating conditions may vary according to the compound that is used to form the ETL. A material for forming the ETL may be any known material that can stably transport electrons injected from an electron injecting electrode (cathode). Examples of materials for forming the ETL include a quinoline derivative, such as tris(8-quinolinorate)aluminum (Alq3), TAZ, BAlq, beryllium bis(benzoquinolin-10-olate) (Bebq$_2$), 9,10-di(naphthalene-2-yl)anthracene (ADN), Compound 201, and Compound 202, but are not limited thereto.

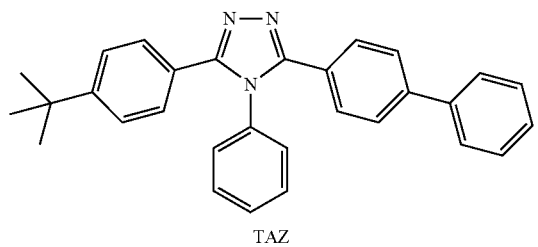

TAZ

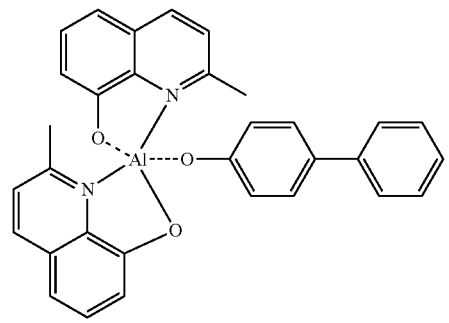

BAlq

Compound 201

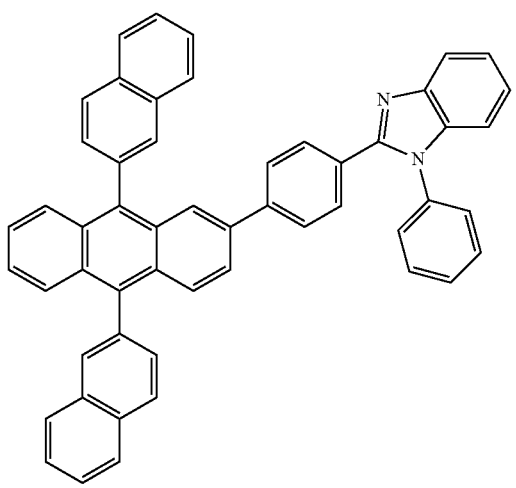

Compound 202

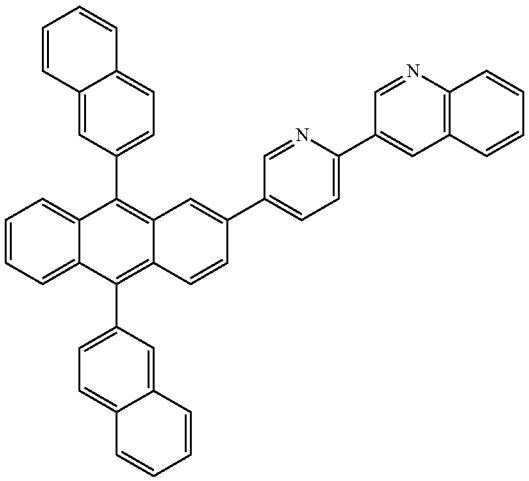

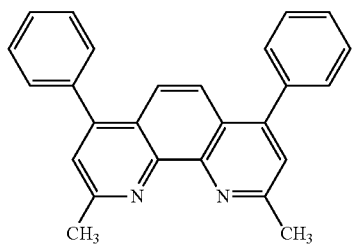

BCP

The thickness of the ETL may be from about 100 Å to about 1,000 Å, and in some embodiments, may be from about 150 Å to about 500 Å. When the thickness of the ETL is within these ranges, the ETL may have satisfactory electron transporting ability without substantially increasing driving voltage.

In some embodiments the ETL may further include a metal-containing material, in addition to the electron-transporting organic compound.

The metal-containing material may include a lithium (Li) complex. Non-limiting examples of the Li complex include lithium quinolate (LiQ) and Compound 203 below.

Compound 203

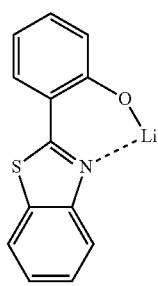

Then, an EIL, which facilitates injection of electrons from the cathode, may be formed on the ETL. Any suitable electron-injecting material may be used to form the EIL.

Examples of materials for forming the EIL include LiF, NaCl, CsF, $Li_2O$, and BaO. The deposition or coating conditions for forming the EIL may be similar to those for the formation of the HIL, though the deposition or coating conditions may vary according to the material that is used to form the EIL.

The thickness of the EIL may be about 1 Å to about 100 Å, for example, about 3 Å to about 90 Å. When the thickness of the EIL is within these ranges, the EIL may have satisfactory electron injection ability without substantially increasing driving voltage.

Finally, the second electrode is disposed on the organic layer. The second electrode may be a cathode that is an electron injection electrode. A metal for forming the second electrode may be a metal, an alloy, an electro-conductive compound (all of which have a low work function), or a mixture thereof. In this regard, the second electrode may be formed of lithium (Li), magnesium (Mg), aluminum (Al), aluminum (Al)-lithium (Li), calcium (Ca), magnesium (Mg)-indium (In), magnesium (Mg)-silver (Ag), or the like, and may be formed as a thin film type transmission electrode. In some embodiments, to manufacture a top-emission light-emitting device, the transmission electrode may be formed of indium tin oxide (ITO) or indium zinc oxide (IZO).

Although the organic light-emitting device of FIG. 1 is described above, the present invention is not limited thereto.

When a phosphorescent dopant is used in the EML, a HBL may be formed between the HTL and the EML or between the H-functional layer and the EML by vacuum deposition, spin coating, casting, Langmuir-Blodgett (LB) deposition, or the like, in order to prevent diffusion of triplet excitons or holes into the ETL. When the HBL is formed using vacuum deposition or spin coating, the conditions for deposition or coating may be similar to those for the formation of the HIL, although the conditions for deposition or coating may vary according to the material that is used to form the HBL. Any known hole-blocking material may be used. Non-limiting examples of hole-blocking materials include oxadiazole derivatives, triazole derivatives, and phenanthroline derivatives. For example, bathocuproine (BCP) represented by the following formula may be used as a material for forming the HBL.

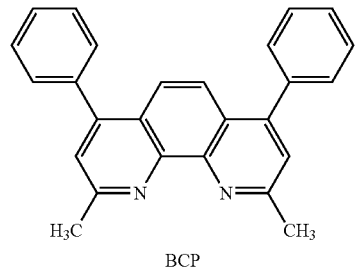

BCP

The thickness of the HBL may be in the range of about 20 Å to about 1000 Å, for example, about 30 Å to about 300 Å. When the thickness of the HBL is within these ranges, the HBL may have a good hole blocking ability without substantially increasing driving voltage.

According to embodiments of the present invention, the organic light-emitting device may be included in various types of flat panel display devices, such as in a passive matrix organic light-emitting display device or in an active matrix organic light-emitting display device. In particular, when the organic light-emitting device is included in an active matrix organic light-emitting display device including a thin-film transistor, the first electrode on the substrate may function as a pixel electrode, and be electrically connected to a source electrode or a drain electrode of the thin-film transistor. Moreover, the organic light-emitting device may also be included in flat panel display devices having double-sided screens.

In some embodiments, the organic layer of the organic light-emitting device may be formed of the compound of Formula 1 by a deposition method or may be formed using a wet method of coating a solution of the compound of Formula 1.

Hereinafter, the present invention will be described with reference to the following synthesis examples and other examples. However, these examples are presented for illustrative purposes only and are not intended to limit the scope of the present invention.

EXAMPLES

Synthesis of Intermediate 1

Intermediates A to F were synthesized according to Reaction Scheme 1 below:

Reaction Scheme 1
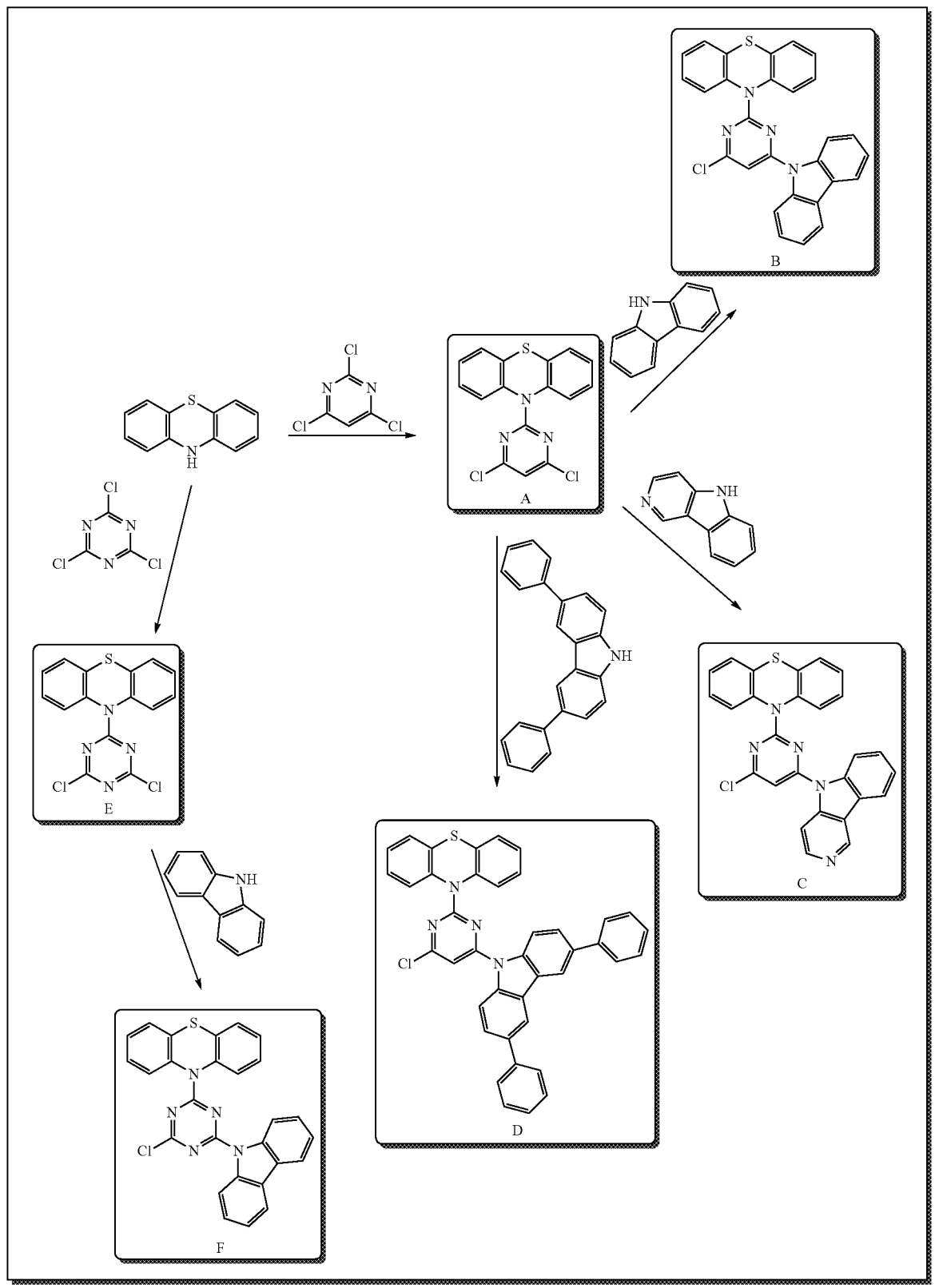

(1) Synthesis of Intermediate A 10 g (1 eq, 0.05 mol) of 10H-phenothiazine, and 10.1 g (4.14 g, 1.1 eq, 0.055 mol) of 2,4,6-trichloropyrimidine were dissolved in 400 ml of toluene. 0.95 g (0.02 eq, 0.001 mmol) of Pd2(dba)3, 8.31 g (1.2 eq, 0.06 mol) of Na(t-bu)O, 0.12 g (0.08 ea, 0.004 mmol) of P(t-Bu)3 were added to the solution, and then heated while stirring for about 12 hours.

The reaction solution from the completed reaction was filtered through Celite, and the filtered product was separated by column chromatography to obtain 9.7 g of Intermediate A with a yield of about 56.4%.

GC-Mass (calc.; 346.23 g/mol. found; 345 g/mol).

<Step 1-1> Synthesis of Intermediate B 20 g (1 eq, 0.057 mol) of Intermediate A, and 10.6 g (1.1 eq, 0.063 mol) 9H-carbazole were dissolved in 400 ml of toluene. 0.97 g (0.02 eq, 0.00114 mmol) of Pd2(dba)3, 8.4 g (1.2 eq, 0.068 mol) of Na(t-bu)O, 0.13 g (0.08 ea, 0.0045 mmol) of P(t-Bu)3 were added to the solution, and then heated while stirring for about 12 hours.

The reaction solution from the completed reaction was filtered through Celite, and the filtered product was separated by column chromatography to obtain 27.18 g of Intermediate B with a yield of about 60.8%.

GC-Mass (calc.; 476.98 g/mol. found; 475 g/mol).

<Step 1-2> Synthesis of Intermediate C 20 g (1 eq, 0.057 mol) of Intermediate A, and 10.59 g (1.1 eq, 0.063 mol) of 5H-pyrido[4,3-b]indole were dissolved in 400 ml of toluene. 0.97 g (0.02 eq, 0.00114 mmol) of Pd2(dba)3, 8.4 g (1.2 eq, 0.068 mol) of Na(t-bu)O, 0.13 g (0.08 ea, 0.0045 mmol) of P(t-Bu)3 were added to the solution, and then heated while stirring for about 12 hours.

The reaction solution from the completed reaction was filtered through Celite, and the filtered product was separated by column chromatography to obtain 14.05 g of Intermediate C with a yield of about 51.6%.

GC-Mass (calc.; 477.97 g/mol. found; 476 g/mol).

<Step 1-3> Synthesis of Intermediate D 20 g (1 eq, 0.057 mol) of Intermediate A, and 20.12 g (1.1 eq, 0.063 mol) 3,6-diphenyl-9H-carbazole were dissolved in 400 ml of toluene. 0.97 g (0.02 eq, 0.00114 mmol) of Pd2(dba)3, 8.4 g (1.2 eq, 0.068 mol) of Na(t-bu)O, 0.13 g (0.08 ea, 0.0045 mmol) of P(t-Bu)3 were added to the solution, and then heated while stirring for about 12 hours.

The reaction solution from the completed reaction was filtered through Celite, and the filtered product was separated by column chromatography to obtain 22.8 g of Intermediate D with a yield of about 63.7%.

GC-Mass (calc.; 629.17 g/mol. found; 628 g/mol).

<Step 2> Synthesis of Intermediate E 10 g (1 eq, 0.05 mol) of 10H-phenothiazine, and 10.14 g (4.14 g, 1.1 eq, 0.055 mol) of 2,4,6-trichloro-1,3,5-triazine were dissolved in 400 ml of toluene. 0.95 g (0.02 eq, 0.001 mmol) of Pd2(dba)3, 8.31 g (1.2 eq, 0.06 mol) of Na(t-bu)O, 0.12 g (0.08 ea, 0.004 mmol) of P(t-Bu)3 were added to the solution, and then heated while stirring for about 12 hours.

The reaction solution from the completed reaction was filtered through Celite, and the filtered product was separated by column chromatography to obtain 12.56 g of Intermediate E with a yield of about 72.4%.

GC-Mass (calc.; 347.22 g/mol. found; 346 g/mol).

<Step 2-1> Synthesis of Intermediate F 20 g (1 eq, 0.0576 mol) of Intermediate A, and 10.6 g (1.1 eq, 0.063 mol) 9H-carbazole were dissolved in 400 ml of toluene. 0.97 g (0.02 eq, 0.00114 mmol) of Pd2(dba)3, 8.4 g (1.2 eq, 0.068 mol) of Na(t-bu)O, 0.13 g (0.08 ea, 0.0045 mmol) of P(t-Bu)3 were added to the solution, and then heated while stirring for about 12 hours.

The reaction solution from the completed reaction was filtered through Celite, and the filtered product was separated by column chromatography to obtain 18.36 g of Intermediate F with a yield of about 66.7%.

GC-Mass (calc.; 477.97 g/mol. found; 476 g/mol).

Intermediate Synthesis 2

Intermediates H to L were synthesized according to Reaction Scheme 2 below:

Reaction Scheme 2
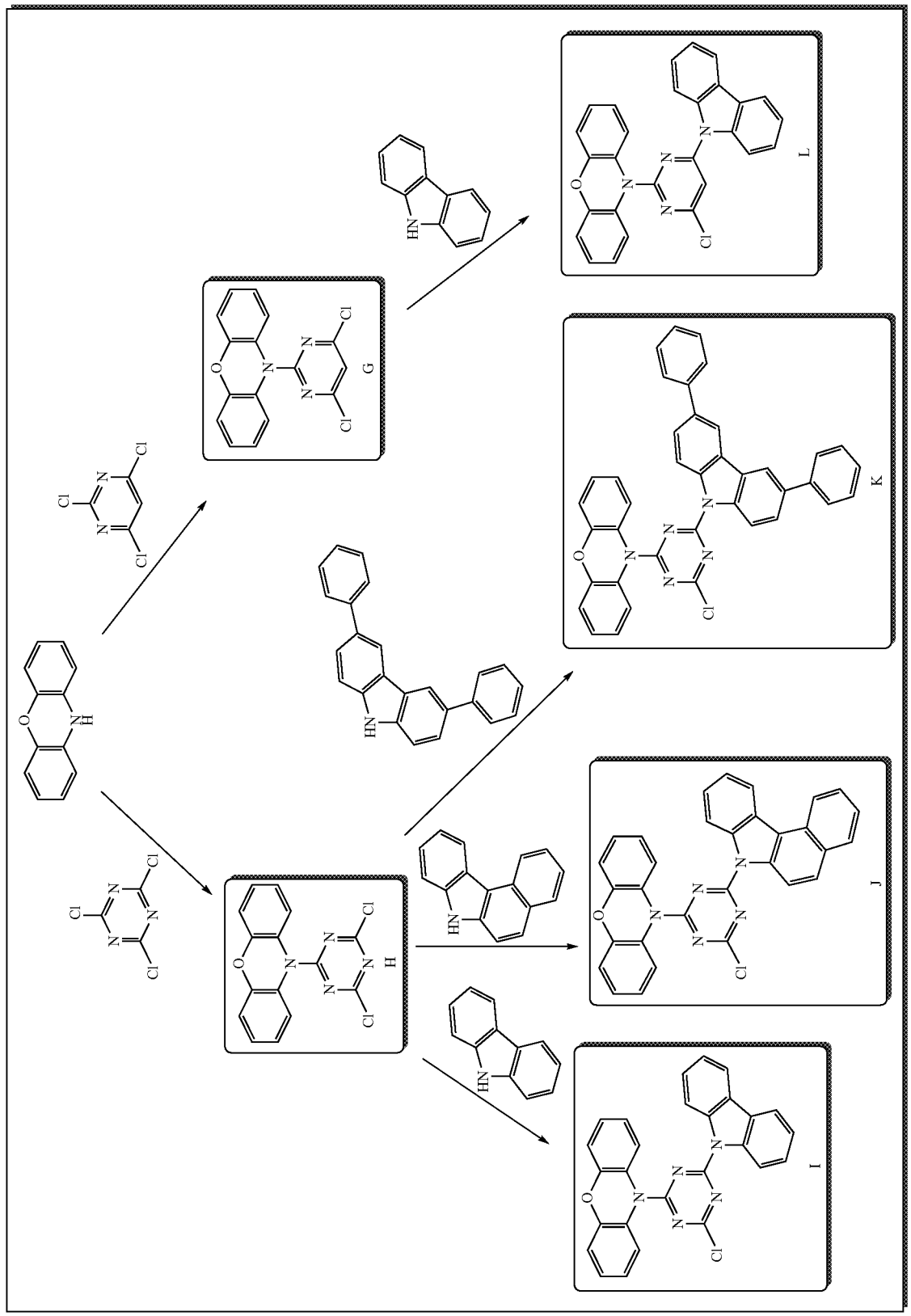

<Step 3> Synthesis of Intermediate H 10 g (1 eq, 0.054 mol) of 10H-phenoxazine and 10.95 g (1.1 eq, 0.059 mol) of 2,4,6-trichloro-1,3,5-triazine were dissolved in 600 ml of toluene. 0.95 g (0.02 eq, 0.001 mmol) of Pd2(dba)3, 8.31 g (1.2 eq, 0.06 mol) of Na(t-bu)O, 0.12 g (0.08 ea, 0.004 mmol) of P(t-Bu)3 were added to the solution, and then heated while stirring for about 12 hours.

The reaction solution from the completed reaction was filtered through Celite, and the filtered product was separated by column chromatography to obtain 9.96 g of Intermediate H with a yield of about 55.7%.

GC-Mass (calc.; 341.16 g/mol. found; 340 g/mol).

<Step 3-1> Synthesis of Intermediate I 10 g (1 eq, 0.0293 mol) of Intermediate H, and 5.38 g (1.1 eq, 0.0322 mol) 9H-carbazole were dissolved in 400 ml of toluene. 0.56 g (0.02 eq, 0.0005 mmol) of Pd2(dba)3, 6.5 g (1.2 eq, 0.035 mol) of Na(t-bu)O, 0.47 g (0.08 ea, 0.0028 mmol) of P(t-Bu)3 were added to the solution, and then heated while stirring for about 12 hours.

The reaction solution from the completed reaction was filtered through Celite, and the filtered product was separated by column chromatography to obtain 8.39 g of Intermediate I with a yield of about 62%.

GC-Mass (calc.; 461.90 g/mol. found; 460 g/mol).

<Step 3-1> Synthesis of Intermediate J 10 g (1 eq, 0.0293 mol) of Intermediate H and 6.99 g (1.1 eq, 0.0322 mol) of 7H-benzo[c]carbazole were dissolved in 500 ml of toluene. 0.56 g (0.02 eq, 0.0005 mmol) of Pd2(dba)3, 6.5 g (1.2 eq, 0.035 mol) of Na(t-bu)O, 0.47 g (0.08 ea, 0.0028 mmol) of P(t-Bu)3 were added to the solution, and then heated while stirring for about 12 hours.

The reaction solution from the completed reaction was filtered through Celite, and the filtered product was separated by column chromatography to obtain 7.8 g of Intermediate J with a yield of about 52%.

GC-Mass (calc.; 511.96 g/mol. found; 510 g/mol).

<Step 3-3> Synthesis of Intermediate K 10 g (1 eq, 0.0293 mol) of Intermediate H, and 10.28 g (1.1 eq, 0.0322 mol) 3,6-diphenyl-9H-carbazole were dissolved in 500 ml of toluene. 0.56 g (0.02 eq, 0.0005 mmol) of Pd2(dba)3, 6.5 g (1.2 eq, 0.035 mol) of Na(t-bu)O, 0.47 g (0.08 ea, 0.0028 mmol) of P(t-Bu)3 were added to the solution, and then heated while stirring for about 12 hours.

The reaction solution from the completed reaction was filtered through Celite, and the filtered product was separated by column chromatography to obtain 9.12 g of Intermediate K with a yield of about 50.7%.

GC-Mass (calc.; 614.09 g/mol. found; 613 g/mol).

<Step 4> Synthesis of Intermediate G 10 g (1 eq, 0.054 mol) of 10H-phenoxazine, and 10.8 g (1.1 eq, 0.059 mol) 2,4,6-trichloropyrimidine were dissolved in 400 ml of toluene. 0.95 g (0.02 eq, 0.001 mmol) of Pd2(dba)3, 8.31 g (1.2 eq, 0.06 mol) of Na(t-bu)O, 0.12 g (0.08 ea, 0.004 mmol) of P(t-Bu)3 were added to the solution, and then heated while stirring for about 12 hours.

The reaction solution from the completed reaction was filtered through Celite, and the filtered product was separated by column chromatography to obtain 9.7 g of Intermediate G with a yield of about 61.9%.

GC-Mass (calc.; 330.17 g/mol. found; 329 g/mol).

<Step 4-1> Synthesis of Intermediate L 10 g (1 eq, 0.03 mol) of Intermediate G, and 5.38 g (1.1 eq, 0.0322 mol) 9H-carbazole were dissolved in 500 ml of toluene. 0.56 g (0.02 eq, 0.0005 mmol) of Pd2(dba)3, 6.5 g (1.2 eq, 0.035 mol) of Na(t-bu)O, 0.47 g (0.08 ea, 0.0028 mmol) of P(t-Bu)3 were added to the solution, and then heated while stirring for about 12 hours.

The reaction solution from the completed reaction was filtered through Celite, and the filtered product was separated by column chromatography to obtain 13.82 g of Intermediate L with a yield of about 66.4%.

GC-Mass (calc.; 460.91 g/mol. found; 459 g/mol).

Synthesis of Compound 1

10 g (1 eq, 0.03 mol) of Intermediate I, and 5.38 g (1.1 eq, 0.0322 mol) of 2-(4,4,5,5-tetramethyl-1,3,2-dioxaborolan-2-yl)pyrimidine were dissolved in 500 ml of toluene in a flask. 1.52 g (0.02 eq, 0.0013 mol) of Pd(PPh3)4 was added into the flask. 400 ml of toluene and 70 ml of a 2M $K_2CO_3$ saturated solution were added into the flask, and stirred under reflux for about 5 hours.

After termination of the reaction, the reaction product was washed and extracted with 400 ml of MC and 150 ml of deionized water. After removing the solvent, the resulting solid product was refined by column chromatography to obtain 14.2 g of Compound 1 with a yield of about 84.5%.

1H NMR: 7.22 (d, 1H), 7.78 (m, 3H), 8.12 (m, 3H), 9.07 (s, 1H).

Elemental Analysis; C, 73.83; H, 3.87; N, 16.14; S, 6.16

Synthesis of Compound 5

10 g (1 eq, 0.03 mol) of Intermediate F, and 7.1 g (1.1 eq, 0.0322 mol) of 3-(4,4,5,5-tetramethyl-1,3,2-dioxaborolan-2-yl)isoquinoline were dissolved in 600 ml of toluene in a flask. 1.52 g (0.02 eq, 0.0013 mol) of Pd(PPh3)4 was added into the flask. 200 ml of toluene and 70 ml of a 2M $K_2CO_3$ saturated solution were added into the flask, and stirred under reflux for about 5 hours.

After termination of the reaction, the reaction product was washed and extracted with 400 ml of MC and 150 ml of deionized water. After removing the solvent, the resulting solid product was refined by column chromatography to obtain 13.9 g of Compound 5 with a yield of about 81.5%.

1H NMR: 8.97 (d, 2H), 8.55 (m, 3H), 7.92 (m, 7H), 7.78 (m, 12H)

Elemental Analysis; C, 75.77; H, 3.89; N, 14.73; S, 5.62

Synthesis of Compound 8

10 g (1 eq, 0.04 mol) of Intermediate B, and 7.5 g (1.1 eq, 0.044 mol) of naphthalen-2-ylboronic acid were dissolved in 200 ml of toluene in a flask. 0.92 g (0.02 eq, 0.0008 mol) of Pd(PPh3)4 was added into the flask. 400 ml of toluene and 50 ml of a 2M $K_2CO_3$ saturated solution were added into the flask, and stirred under reflux for about 5 hours.

After termination of the reaction, the reaction product was washed and extracted with 400 ml of MC and 150 ml of deionized water. After removing the solvent, the resulting solid product was refined by column chromatography to obtain 17.5 g of Compound 8 with a yield of about 77.4%.

GC-Mass (calc.; 568.17 g/mol. found; 567 g/mol).

Elemental Analysis; C, 80.26; H, 4.25; N, 9.85; S, 5.64

Synthesis of Compound 11

10 g (1 eq, 0.03 mol) of Intermediate D, and 5.38 g (1.1 eq, 0.0322 mol) of 2-(4,4,5,5-tetramethyl-1,3,2-dioxaborolan-2-yl)pyridine were dissolved in 500 ml of toluene in a flask. 1.52 g (0.02 eq, 0.0013 mol) of Pd(PPh3)4 was added into the flask. 400 ml of toluene and 70 ml of a 2M $K_2CO_3$ saturated solution were added into the flask, and stirred under reflux for about 5 hours.

After termination of the reaction, the reaction product was washed and extracted with 400 ml of MC and 150 ml of deionized water. After removing the solvent, the resulting solid product was refined by column chromatography to obtain 14.2 g of Compound 11 with a yield of about 84.5%.

1H NMR: 7.22 (d, 1H), 7.78 (m, 3H), 8.12 (m, 3H), 9.07 (s, 1H).

Synthesis of Compound 15

10 g (1 eq, 0.03 mol) of Intermediate F, and 7.1 g (1.1 eq, 0.0322 mol) of naphthalen-1-ylboronic acid were dissolved in 600 ml of toluene in a flask. 1.52 g (0.02 eq, 0.0013 mol) of Pd(PPh3)4 was added into the flask. 200 ml of toluene and 70 ml of a 2M $K_2CO_3$ saturated solution were added into the flask, and stirred under reflux for about 5 hours.

After termination of the reaction, the reaction product was washed and extracted with 400 ml of MC and 150 ml of deionized water. After removing the solvent, the resulting solid product was refined by column chromatography to obtain 14.2 g of Compound 15 with a yield of about 84.5%.

1H NMR; 6.99 (t, 2H), 7.22 (m, 9H), 7.78 (m, 4H), 8.12 (m, 5H), 9.07 (t, 2H).

Elemental Analysis; C, 78.01; H, 4.07; N, 12.29; S, 5.63

Synthesis of Compound 21

10 g (1 eq, 0.03 mol) of Intermediate L, and 5.1 g (1.1 eq, 0.0322 mol) of isoquinolin-3-ylboronic acid were dissolved in 500 ml of toluene in a flask. 1.52 g (0.02 eq, 0.0013 mol) of Pd(PPh3)4 was added into the flask. 400 ml of toluene and 70 ml of a 2M $K_2CO_3$ saturated solution were added into the flask, and stirred under reflux for about 5 hours.

After termination of the reaction, the reaction product was washed and extracted with 400 ml of MC and 150 ml of deionized water. After removing the solvent, the resulting solid product was refined by column chromatography to obtain 12.7 g of Compound 21 with a yield of about 79%.

1H NMR: 6.78 (t, 2H), 7.22 (m, 6H), 7.42 (m, 6H), 7.78 (m, 5H), 8.12 (d, 1H), 9.07 (s, 1H).

Elemental Analysis; C, 80.27; H, 4.19; N, 12.65; O, 2.89

Synthesis of Compound 26

10 g (1 eq, 0.03 mol) of Intermediate I, and 4.7 g (1.1 eq, 0.0322 mol) of 2-(4,4,5,5-tetramethyl-1,3,2-dioxaborolan-2-yl)pyridine were dissolved in 500 ml of toluene in a flask. 1.52 g (0.02 eq, 0.0013 mol) of Pd(PPh3)4 was added into the flask. 400 ml of toluene and 70 ml of a 2M $K_2CO_3$ saturated solution were added into the flask, and stirred under reflux for about 5 hours.

After termination of the reaction, the reaction product was washed and extracted with 400 ml of MC and 150 ml of deionized water. After removing the solvent, the resulting solid product was refined by column chromatography to obtain 14.2 g of Compound 26 with a yield of about 84.5%.

1H NMR: 6.99 (t, 2H), 7.22 (m, 6H), 7.52 (m, 5H), 7.78 (m, 4H), 8.12 (m, 1H), 9.07 (t, 2H).

Elemental Analysis; C, 76.18; H, 4.00; N, 16.66; O, 3.17

Synthesis of Compound 27

10 g (1 eq, 0.03 mol) of Intermediate I, and 4.7 g (1.1 eq, 0.0322 mol) of 2-(4,4,5,5-tetramethyl-1,3,2-dioxaborolan-2-yl)pyridine were dissolved in 500 ml of toluene in a flask. 1.52 g (0.02 eq, 0.0013 mol) of Pd(PPh3)4 was added into the flask. 400 ml of toluene and 70 ml of a 2M $K_2CO_3$ saturated solution were added into the flask, and stirred under reflux for about 5 hours.

After termination of the reaction, the reaction product was washed and extracted with 400 ml of MC and 150 ml of deionized water. After removing the solvent, the resulting solid product was refined by column chromatography to obtain 13.6 g of Compound 26 with a yield of about 81.5%.

1H NMR: 6.99 (t, 2H), 7.22 (m, 6H), 7.52 (m, 5H), 7.78 (m, 4H), 8.12 (m, 1H), 9.07 (t, 2H).

Elemental Analysis; C, 80.47; H, 4.30; N, 12.80; O, 2.44

Synthesis of Compound 28

10 g (1 eq, 0.03 mol) of Intermediate J, and 5.38 g (1.1 eq, 0.0322 mol) of 2-(4,4,5,5-tetramethyl-1,3,2-dioxaborolan-2-yl)pyridine were dissolved in 500 ml of toluene in a flask. 1.52 g (0.02 eq, 0.0013 mol) of Pd(PPh3)4 was added into the flask. 400 ml of toluene and 70 ml of a 2M $K_2CO_3$ saturated solution were added into the flask, and stirred under reflux for about 5 hours.

After termination of the reaction, the reaction product was washed and extracted with 400 ml of MC and 150 ml of deionized water. After removing the solvent, the resulting solid product was refined by column chromatography to obtain 22.7 g of Compound 28 with a yield of about 87.1%.

1H NMR: 6.89 (t, 2H), 7.2 (m, 5H), 7.49 (m, 7H), 7.9 (m, 3H), 8.22 (m, 2H)

Elemental Analysis; C, 77.96; H, 4.00; N, 15.15; O, 2.88

Synthesis of Compound 30

10 g (1 eq, 0.03 mol) of Intermediate C, and 2.7 g (1.1 eq, 0.0322 mol) of phenyl boronic acid were dissolved in 400 ml of toluene in a flask. 1.34 g (0.02 eq, 0.001 mol) of Pd(PPh3)4 was added into the flask. 250 ml of toluene and 50 ml of a 2M $K_2CO_3$ saturated solution were added into the flask, and stirred under reflux for about 5 hours.

After termination of the reaction, the reaction product was washed and extracted with 400 ml of MC and 150 ml of deionized water. After removing the solvent, the resulting solid product was refined by column chromatography to obtain 17.7 g of Compound 30 with a yield of about 91%.

1H NMR: 6.97 (m, 2H), 7.22 (m, 24H), 7.78 (d, 1H), 8.12 (m, 4H), 9.07 (s, 1H).

Elemental Analysis; C, 73.83; H, 3.87; N, 16.14; S, 6.16

Synthesis of Compound 32

10 g (1 eq, 0.03 mol) of Intermediate L, and 5.8 g (1.1 eq, 0.033 mol) of phenanthren-9-ylboronic acid were dissolved in 500 ml of toluene in a flask. 1.52 g (0.02 eq, 0.0013 mol) of Pd(PPh3)4 was added into the flask. 500 ml of toluene and 70 ml of a 2M $K_2CO_3$ saturated solution were added into the flask, and stirred under reflux for about 5 hours.

After termination of the reaction, the reaction product was washed and extracted with 400 ml of MC and 150 ml of deionized water. After removing the solvent, the resulting solid product was refined by column chromatography to obtain 14.2 g of Compound 32 with a yield of about 84.5%.

1H NMR: 7.10 (m, 10H), 7.78 (d, 1H), 8.10 (m, 8H), 8.47, (d, 1H), 8.55 (d, 1H), 8.98 (d, 2H), 9.07 (s, 1H).

Elemental Analysis; C, 77.40; H, 3.90; N, 13.54; S, 5.17

Synthesis of Compound 34

10 g (1 eq, 0.03 mol) of Intermediate L, and 6.2 g (1.1 eq, 0.0322 mol) of pyren-4-ylboronic acid were dissolved in 600 ml of toluene in a flask. 1.52 g (0.02 eq, 0.0013 mol) of Pd(PPh3)4 was added into the flask. 600 ml of toluene and 90 ml of a 2M $K_2CO_3$ saturated solution were added into the flask, and stirred under reflux for about 5 hours.

After termination of the reaction, the reaction product was washed and extracted with 400 ml of MC and 150 ml of deionized water. After removing the solvent, the resulting solid product was refined by column chromatography to obtain 12.9 g of Compound 34 with a yield of about 81.4%.

1H NMR: 7.10 (m, 2H), 7.62 (m, 8H), 7.88 (d, 1H), 7.99 (m, 6H), 8.12 (d, 1H), 8.47, (d, 1H), 8.55 (d, 1H), 9.07 (s, 1H).

Elemental Analysis; C, 78.24; H, 3.75; N, 13.03; S, 4.97

Example 1

To manufacture an anode, a corning 15 Ω/$cm^2$ (500 Å) ITO glass substrate was cut to a size of 50 mm×50 mm×0.5 mm and then sonicated in isopropyl alcohol and pure water each for 10 minutes, and then cleaned by irradiation with ultraviolet rays for 10 minutes and exposure to ozone. The resulting glass substrate was loaded into a vacuum deposition device.

Then, 2-TNATA, which is a HIL material, was vacuum-deposited on the glass substrate to form a HIL having a thickness of about 600 Å. Then, 4,4'-bis[N-(1-naphthyl)-N-phenylamino]biphenyl (NPB), which is a hole transporting compound, was vacuum-deposited on the HIL to form a HTL having a thickness of about 300 Å.

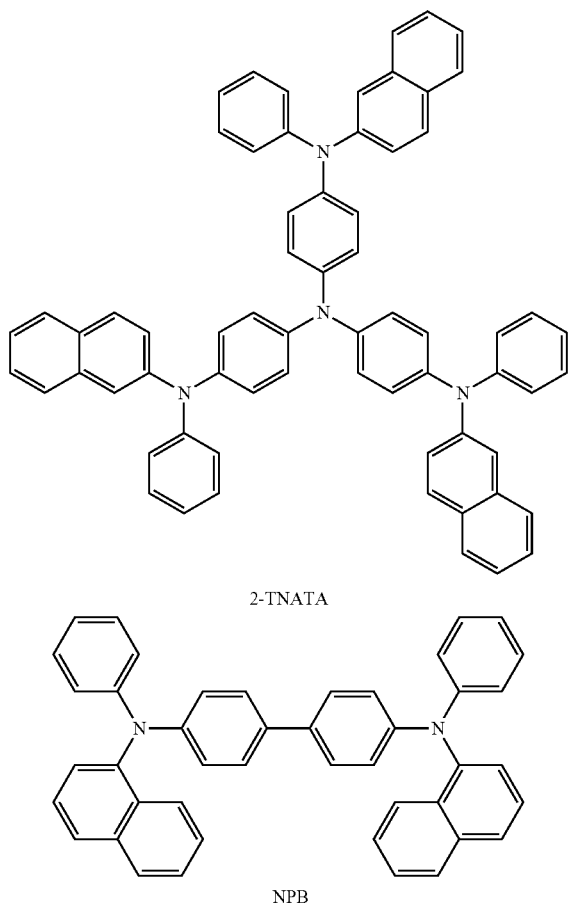

2-TNATA

NPB

Then, a green fluorescent host Ir(PPy)3 and Compound 1 were deposited at the same time in a weight ratio of 13:87 on the HTL, to form an EML with a thickness of 300 Å. Next, Alq$_3$ was deposited on the EML to form an ETL having a thickness of about 300 Å, and Al was deposited to a thickness of 1200 Å to form an Al electrode (cathode), thereby completing the manufacture of an organic light-emitting device.

The organic light-emitting device had a driving voltage of 3.6V at a current density of 5.4 mA/cm$^2$, a high luminosity of 3500 cd/m$^2$, color coordinates of (0.32, 0.62), and a luminescent efficiency of 68.5 cd/A.

Example 2

An organic light-emitting device was manufactured in the same manner as in Example 1, except that Compound 5 instead of Compound 1 was used to form the EML.

The organic light-emitting device had a driving voltage of 4.2V at a current density of 5.9 mA/cm$^2$, a high luminosity of 3500 cd/m$^2$, color coordinates of (0.32, 0.63), and a luminescent efficiency of 58.9 cd/A.

Example 3

An organic light-emitting device was manufactured in the same manner as in Example 1, except that Compound 8 instead of Compound 1 was used to form the EML.

The organic light-emitting device had a driving voltage of 4.0V at a current density of 5.9 mA/cm$^2$, a high luminosity of 3500 cd/m$^2$, color coordinates of (0.33, 0.63), and a luminescent efficiency of 60.7 cd/A.

Example 4

An organic light-emitting device was manufactured in the same manner as in Example 1, except that Compound 11 instead of Compound 1 was used to form the EML.

The organic light-emitting device had a driving voltage of 3.6V at a current density of 5.9 mA/cm$^2$, a high luminosity of 3500 cd/m$^2$, color coordinates of (0.34, 0.61), and a luminescent efficiency of 69.3 cd/A.

Example 5

An organic light-emitting device was manufactured in the same manner as in Example 1, except that Compound 15 instead of Compound 1 was used to form the EML.

The organic light-emitting device had a driving voltage of 3.6V at a current density of 5.4 mA/cm$^2$, a high luminosity of 3500 cd/m$^2$, color coordinates of (0.33, 0.62), and a luminescent efficiency of 64.7 cd/A.

Example 6

An organic light-emitting device was manufactured in the same manner as in Example 1, except that Compound 21 instead of Compound 1 was used to form the EML.

The organic light-emitting device had a driving voltage of 4.2V at a current density of 5.9 mA/cm$^2$, a high luminosity of 3500 cd/m$^2$, color coordinates of (0.31, 0.60), and a luminescent efficiency of 64.6 cd/A.

Example 7

An organic light-emitting device was manufactured in the same manner as in Example 1, except that Compound 26 instead of Compound 1 was used to form the EML.

The organic light-emitting device had a driving voltage of 3.9V at a current density of 5.5 mA/cm$^2$, a high luminosity of 3500 cd/m$^2$, color coordinates of (0.32, 0.60), and a luminescent efficiency of 70.4 cd/A.

Example 8

An organic light-emitting device was manufactured in the same manner as in Example 1, except that Compound 27 instead of Compound 1 was used to form the EML.

The organic light-emitting device had a driving voltage of 3.6V at a current density of 5.4 mA/cm$^2$, a high luminosity of 3500 cd/m$^2$, color coordinates of (0.32, 0.62), and a luminescent efficiency of 66.5 cd/A.

Example 9

An organic light-emitting device was manufactured in the same manner as in Example 1, except that Compound 28 instead of Compound 1 was used to form the EML.

The organic light-emitting device had a driving voltage of 4.1V at a current density of 5.2 mA/cm$^2$, a high luminosity of 3500 cd/m$^2$, color coordinates of (0.31, 0.61), and a luminescent efficiency of 67.4 cd/A.

Example 10

An organic light-emitting device was manufactured in the same manner as in Example 1, except that Compound 30 instead of Compound 1 was used to form the EML.

The organic light-emitting device had a driving voltage of 4.7V at a current density of 5.8 mA/cm$^2$, a high luminosity of 3500 cd/m$^2$, color coordinates of (0.30, 0.62), and a luminescent efficiency of 55.7 cd/A.

Example 11

An organic light-emitting device was manufactured in the same manner as in Example 1, except that Compound 32 instead of Compound 1 was used to form the EML.

The organic light-emitting device had a driving voltage of 3.9V at a current density of 5.2 mA/cm², a high luminosity of 3500 cd/m², color coordinates of (0.31, 0.65), and a luminescent efficiency of 62.1 cd/A.

Example 12

An organic light-emitting device was manufactured in the same manner as in Example 1, except that Compound 34 instead of Compound 1 was used to form the EML.

The organic light-emitting device had a driving voltage of 4.32V at a current density of 5.7 mA/cm², a high luminosity of 3500 cd/m², color coordinates of (0.31, 0.64), and a luminescent efficiency of 69.8 cd/A.

Comparative Example 1

An organic light-emitting device was manufactured in the same manner as in Example 1, except that CBP as a common material, instead of Compound 1, was used to form the EML.

The organic light-emitting device had a driving voltage of 5.1V at a current density of 6.2 mA/cm², a high luminosity of 3500 cd/m², color coordinates of (0.32, 0.62), which are almost the same as those of Examples 1-12, and a luminescent efficiency of 51.2 cd/A.

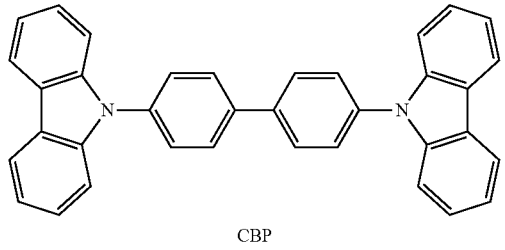 [SMILES: c1ccc2c(c1)c1ccccc1n2-c1ccc(-c2ccc(-n3c4ccccc4c4ccccc43)cc2)cc1 ; "CBP"]

CBP

The characteristics and lifetimes of the organic light-emitting devices of Examples 1-12 and Comparative Example 1 are shown in Table 1 below.

The organic light-emitting devices including an ETL or EML manufactured using Compounds 1 to 34 as a phosphorescent host in Examples 1 to 12 had driving voltages lower by 20% or greater than the devices manufactured using CBP, and thus had higher efficiency and good I-V-L characteristics. In particular, the lifetime characteristics were markedly improved by 70% or greater in the organic light-emitting devices of Examples 1 to 11, as compared to the organic light-emitting device of Comparative Example 1.

The novel compounds of Formula 1 described above may be used as green phosphorescent hosts with high luminescence characteristics. Therefore, organic light-emitting devices having high efficiency, low driving voltages, high luminance, and long lifetimes may be manufactured using the compounds.

The compound of Formula 1, having a heterocyclic group in the molecule, has a high glass transition temperature (Tg) or a high melting point due to the inclusion of the heterocyclic group. Thus, the heterocyclic compound has high heat resistance against Joule's heat generated in organic layers, or between an organic layer and a metal electrode when light emission occurs, and has good durability in high-temperature environments. An organic light-emitting device manufactured using the compound of Formula 1 described above may have good durability when stored or operated.

While the present invention has been illustrated and described with reference to exemplary embodiments thereof, it will be understood by those of ordinary skill in the art that various changes may be made to the described embodiments without departing from the spirit and scope of the present invention as defined by the following claims.

TABLE 1

| | Green EMI (host) | Driving Voltage (V) | Current density (mA/cm²) | Luminosity (cd/m²) | Luminescent Efficiency (cd/A) | Color coordinates | Half-Life span (hr) |
|---|---|---|---|---|---|---|---|
| Ex. 1 | Comp. 1 | 3.6 | 5.4 | 3500 | 68.5 | (0.32, 0.62) | 340 |
| Ex. 2 | Comp. 5 | 4.2 | 5.9 | 3500 | 58.9 | (0.32, 0.63) | 299 |
| Ex. 3 | Comp. 8 | 4.0 | 5.9 | 3500 | 60.7 | (0.33, 0.63) | 357 |
| Ex. 4 | Comp. 11 | 3.6 | 5.9 | 3500 | 69.3 | (0.34, 0.61) | 397 |
| Ex. 5 | Comp. 15 | 3.6 | 5.4 | 3500 | 64.7 | (0.33, 0.62) | 385 |
| Ex. 6 | Comp. 21 | 3.9 | 5.5 | 3500 | 70.4 | (0.32, 0.60) | 326 |
| Ex. 7 | Comp. 26 | 3.6 | 5.4 | 3500 | 66.5 | (0.32, 0.62) | 339 |
| Ex. 8 | Comp. 27 | 4.2 | 5.9 | 3500 | 64.6 | (0.31, 0.60) | 291 |
| Ex. 9 | Comp. 28 | 4.1 | 5.2 | 3500 | 67.4 | (0.31, 0.61) | 228 |
| Ex. 10 | Comp. 30 | 4.7 | 5.8 | 3500 | 55.7 | (0.30, 0.62) | 318 |
| Ex. 11 | Comp. 32 | 3.9 | 5.2 | 3500 | 62.1 | (0.31, 0.65) | 281 |
| Ex. 12 | Comp. 34 | 4.32 | 5.7 | 3500 | 69.8 | (0.31, 0.64) | 322 |
| Comp. Ex. 1 | CBP | 5.1 | 5.1 | 3500 | 51.2 | (0.32, 0.62) | 174 |

What is claimed is:
1. A compound represented by Formula 1:

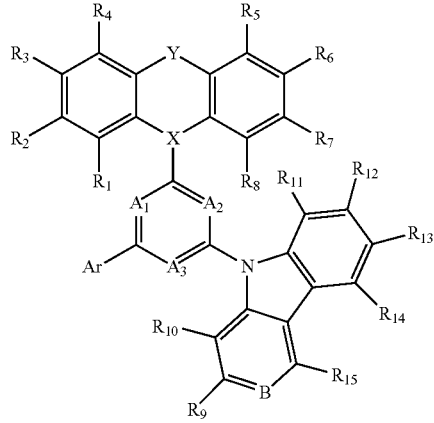

wherein:
$A_1$ to $A_3$ are each independently N or $C(R_{20})$;
X is N;
Y is O or S;
B is N or $C(R_{21})$;
Ar is a substituted or unsubstituted $C_6$-$C_{60}$ aryl group or a substituted or unsubstituted $C_3$-$C_{30}$ heteroaryl group;
$R_1$ to $R_{15}$, $R_{20}$, and $R_{21}$ are each independently a hydrogen atom, a deuterium atom, a substituted or unsubstituted C1-C60 alkyl group, a substituted or unsubstituted C3-C60 cycloalkyl group, a substituted or unsubstituted C6-C60 aryl group, or a substituted or unsubstituted C3-C60 heteroaryl group, and $R_{15}$ and $R_{21}$ optionally combine to form a ring; and

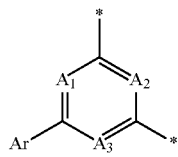

is a moiety represented by one of the following formulae, wherein * indicates a binding site:

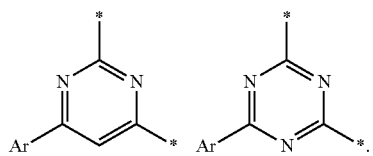

2. The compound of claim 1, wherein, in Formula 1,

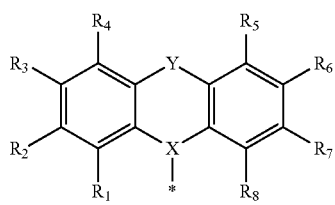

is a moiety represented by one of the following formulae, wherein * indicates a binding site:

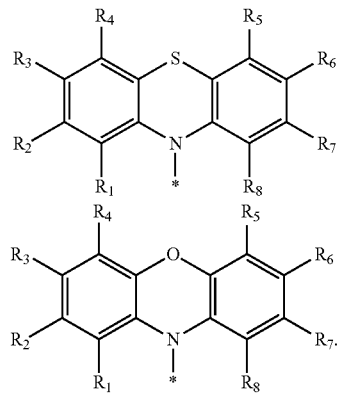

3. The compound of claim 1, wherein, in Formula 1,

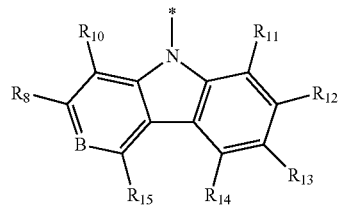

is a moiety represented by one of the following formulae:

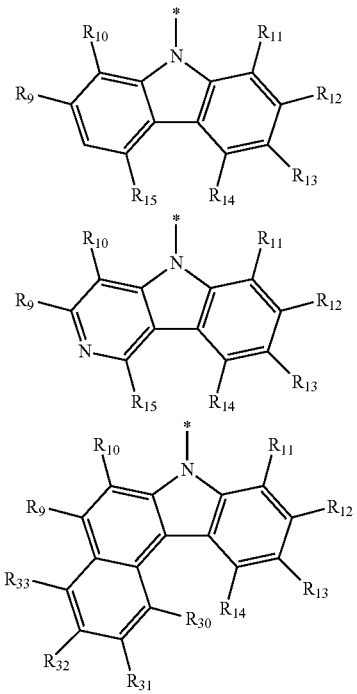

wherein, $R_{30}$ to $R_{33}$ are each independently a hydrogen atom, a deuterium atom, a substituted or unsubstituted C1-C60 alkyl group, a substituted or unsubstituted C3-C60 cycloalkyl group, a substituted or unsubstituted C6-C60 aryl group, or a substituted or unsubstituted C3-C60 heteroaryl group; and * indicates a binding site.

4. The compound of claim 1, wherein, in Formula 1, Ar is a compound represented by one of the following formulae, wherein * indicates a binding site:

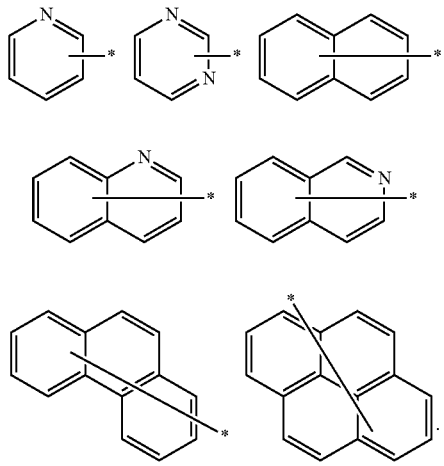

5. The compound of claim 1, wherein, in Formula 1, $R_1$ to $R_8$ are each independently a hydrogen atom or a deuterium atom; and $R_9$ to $R_{15}$, and $R_{21}$ are each independently a hydrogen atom, a deuterium atom or a substituted or unsubstituted C6-C60 aryl group.

6. The compound of claim 1, wherein the compound of Formula 1 is one of Compounds 1 through 34:

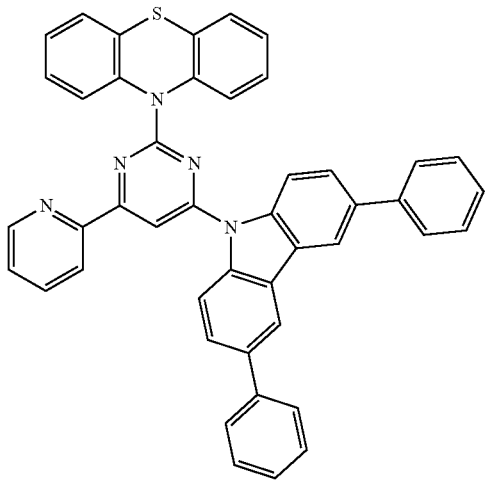

-continued

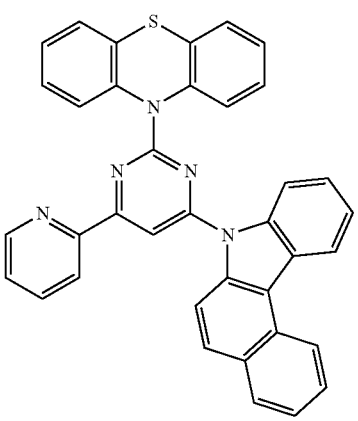

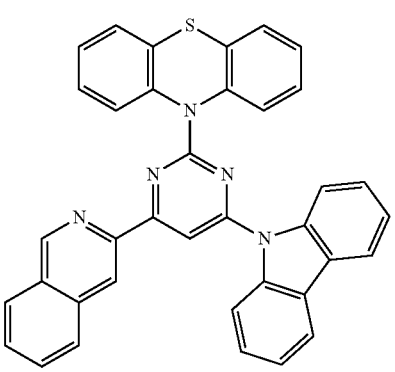

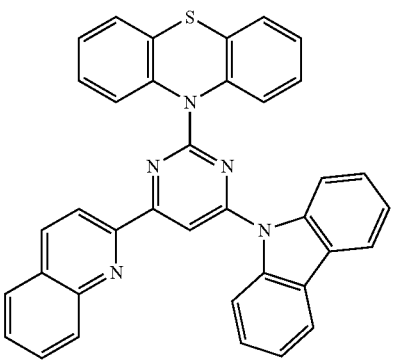

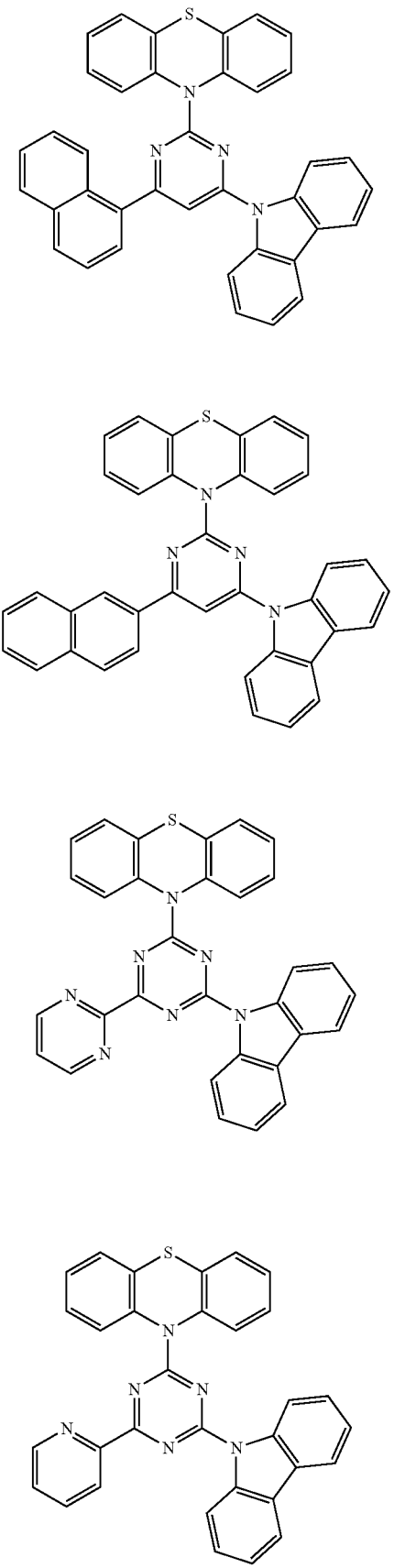
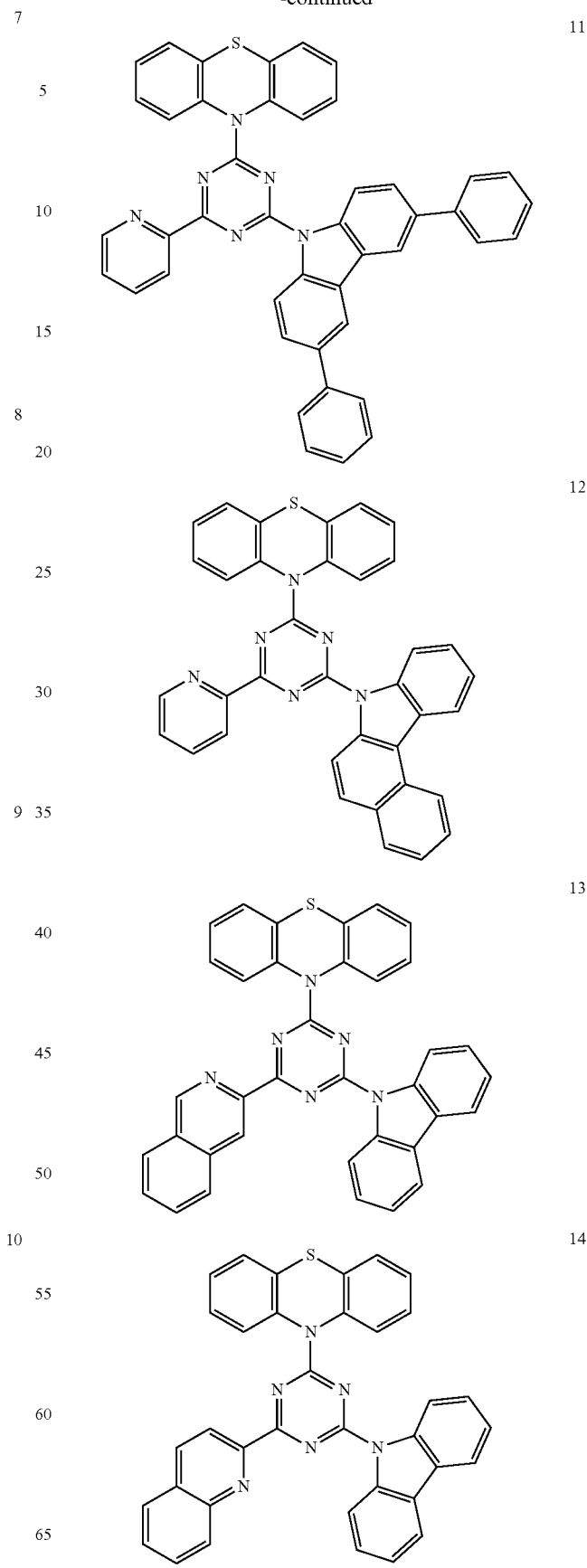

15
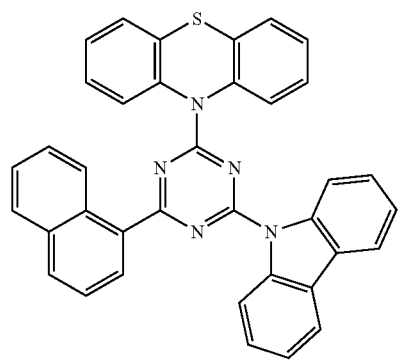
16
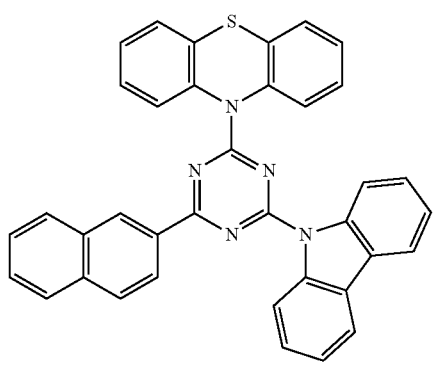
17
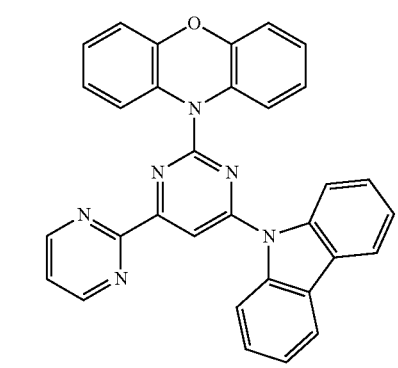
18
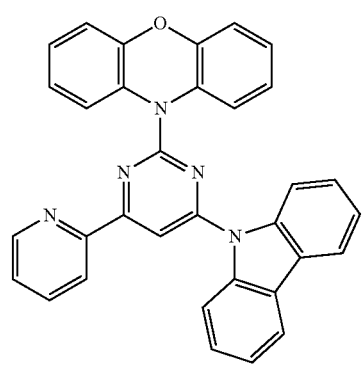
19
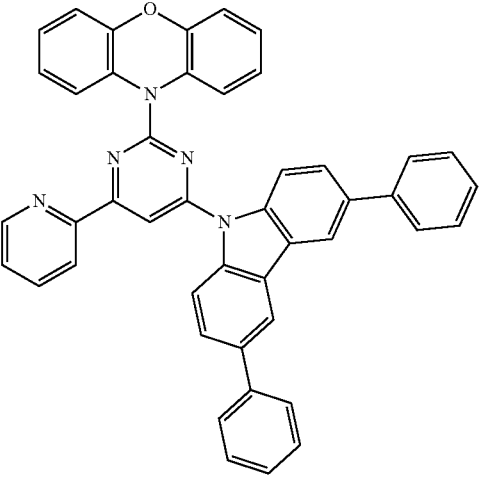
20
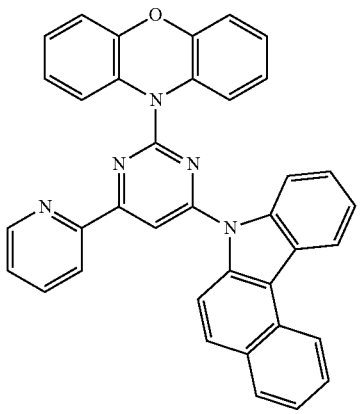
21
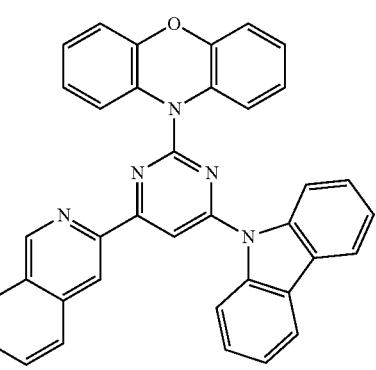
22

87
-continued
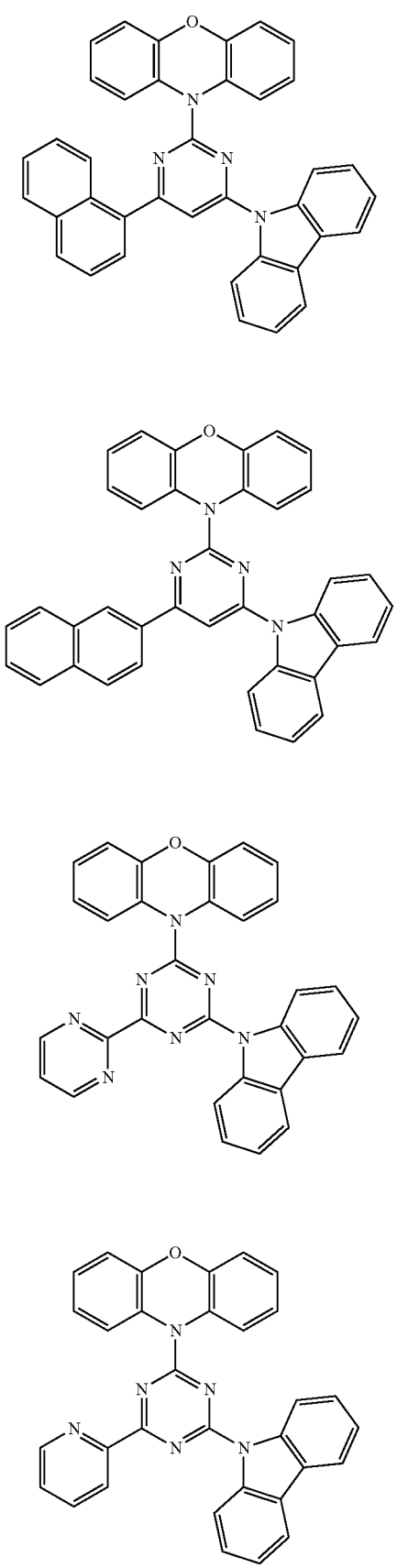
88
-continued
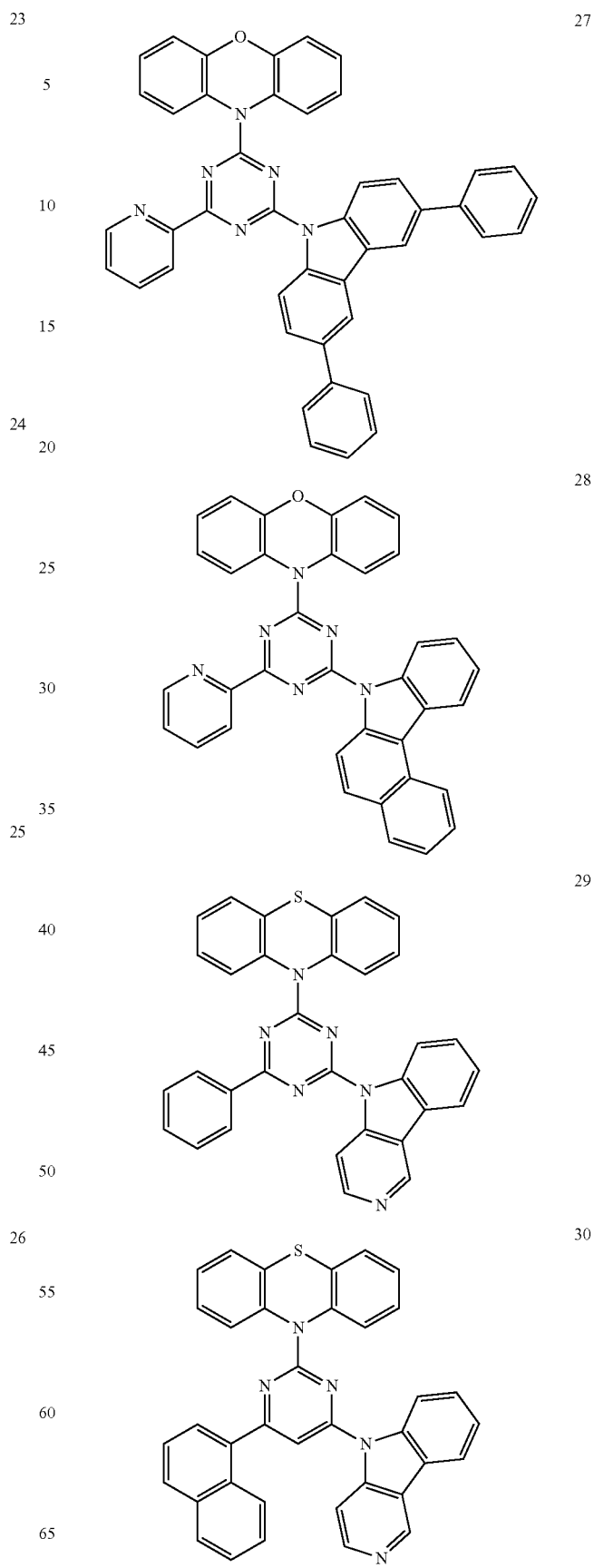

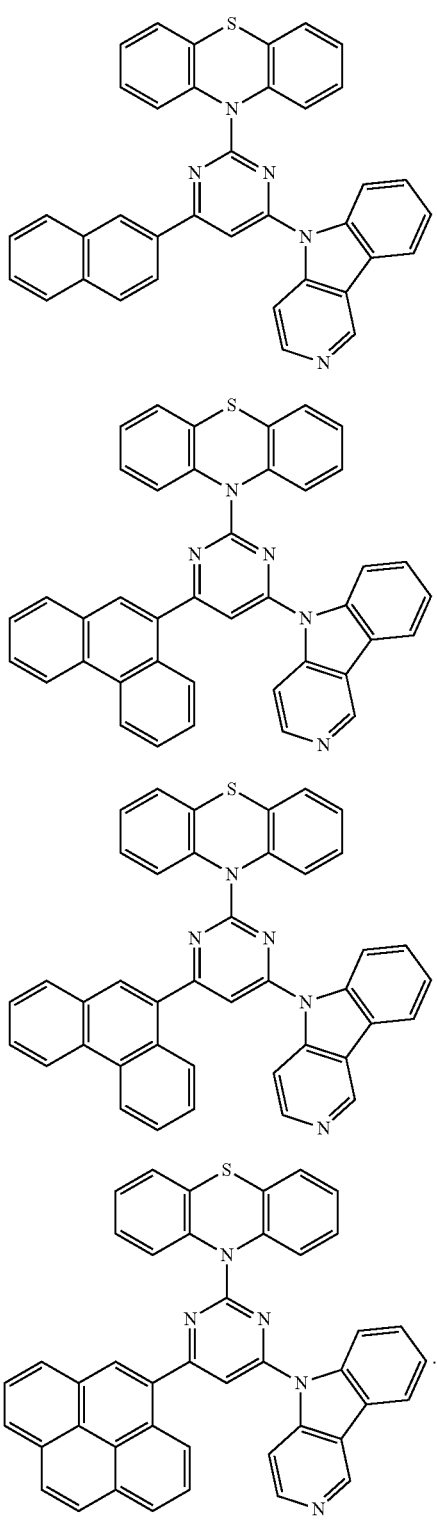

7. An organic light-emitting device comprising: a first electrode; a second electrode; and an organic layer between the first electrode and the second electrode, wherein the organic layer comprises the compound according to claim 1.

8. The organic light-emitting device of claim 7, wherein the organic layer comprises an emission layer.

9. The organic light-emitting device of claim 7, wherein the organic layer comprises an emission layer, and the compound represented by Formula 1 is a host in a fluorescent or phosphorescent device.

10. The organic light-emitting device of claim 7, wherein the organic light-emitting device comprises an electron injection layer, an electron transport layer, an emission layer, a hole injection layer, a hole transport layer, or a functional layer having both hole injection and transport capabilities; and the emission layer comprises the compound represented by Formula 1 and an anthracene-based compound.

11. The organic light-emitting device of claim 7, wherein the organic light-emitting device comprises an electron injection layer, an electron transport layer, an emission layer, a hole injection layer, a hole transport layer, or a functional layer having both hole injection and transport capabilities; and the emission layer comprises the compound represented by Formula 1 and an arylamine-based compound.

12. The organic light-emitting device of claim 7, wherein the organic light-emitting device comprises an electron injection layer, an electron transport layer, an emission layer, a hole injection layer, a hole transport layer, or a functional layer having both hole injection and transport capabilities; and the emission layer comprises the compound represented by Formula 1 and a styryl-based compound.

13. The organic light-emitting device of claim 7, wherein the organic light-emitting device comprises an electron injection layer, an electron transport layer, an emission layer, a hole injection layer, a hole transport layer, or a functional layer having both hole injection and transport capabilities; and at least one of a red emission layer, a green emission layer, a blue emission layer, and a white emission layer of the emission layer comprises a phosphorescent compound.

14. The organic light-emitting device of claim 13, wherein at least one of the hole injection layer, the hole transport layer, and the functional layer having both hole injection and hole transport capabilities further comprises a charge-generating material.

15. The organic light-emitting device of claim 14, wherein the charge-generating material is a p-dopant, and the p-dopant is a quinone derivative, a metal oxide or a cyano group-containing compound.

16. The organic light-emitting device of claim 7, wherein the organic layer further comprises an electron transport layer, and the electron transport layer comprises an electron transporting organic compound and a metal complex.

17. The organic light-emitting device of claim 16, wherein the metal complex is a Li complex.

18. The organic light-emitting device of claim 7, wherein the organic layer is formed from the compound represented by Formula 1 using a wet process.

19. A flat panel display device comprising the organic light-emitting device of claim 7, wherein the first electrode of the organic light-emitting device is electrically connected to a source electrode or a drain electrode of a thin-film transistor.

* * * * *